US011406715B2

(12) United States Patent
Guardino et al.

(10) Patent No.: US 11,406,715 B2
(45) Date of Patent: Aug. 9, 2022

(54) METHODS OF TREATING HER2-POSITIVE METASTATIC BREAST CANCER

(71) Applicant: Genentech, Inc., South San Francisco, CA (US)

(72) Inventors: Alice Elizabeth Guardino, South San Francisco, CA (US); Meghna Samant, South San Francisco, CA (US); Alexander Strasak, South San Francisco, CA (US); Melanie Smitt, South San Francisco, CA (US); Monika Patre, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 38 days.

(21) Appl. No.: 15/576,593

(22) PCT Filed: May 27, 2016

(86) PCT No.: PCT/US2016/034835
§ 371 (c)(1),
(2) Date: Nov. 22, 2017

(87) PCT Pub. No.: WO2016/196373
PCT Pub. Date: Dec. 8, 2016

(65) Prior Publication Data
US 2019/0030181 A1 Jan. 31, 2019

Related U.S. Application Data

(60) Provisional application No. 62/168,809, filed on May 30, 2015.

(51) Int. Cl.
A61K 39/39 (2006.01)
A61K 47/68 (2017.01)
C07K 16/32 (2006.01)
A61K 31/395 (2006.01)
A61K 31/337 (2006.01)
A61K 39/395 (2006.01)
A61P 35/04 (2006.01)
A61K 39/00 (2006.01)

(52) U.S. Cl.
CPC ........ *A61K 47/6855* (2017.08); *A61K 31/337* (2013.01); *A61K 31/395* (2013.01); *A61K 39/39558* (2013.01); *A61K 47/6803* (2017.08); *A61P 35/04* (2018.01); *C07K 16/32* (2013.01); *A61K 2039/507* (2013.01)

(58) Field of Classification Search
CPC .......... A61K 47/6855; A61K 39/39558; A61K 47/6803; A61K 2039/507; A61P 35/04; C07K 16/32
See application file for complete search history.

(56) References Cited

U.S. PATENT DOCUMENTS

| | | |
|---|---|---|
| 4,968,603 A | 11/1990 | Slamon et al. |
| 5,208,020 A | 5/1993 | Chari et al. |
| 5,648,237 A | 7/1997 | Carter |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,821,337 A | 10/1998 | Carter et al. |
| 6,015,567 A | 1/2000 | Hudziak et al. |
| 6,054,297 A | 4/2000 | Carter et al. |
| 6,127,526 A | 10/2000 | Blank |
| 6,165,464 A | 12/2000 | Hudziak et al. |
| 6,267,958 B1 | 7/2001 | Andya et al. |
| 6,333,169 B1 | 12/2001 | Hudziak et al. |
| 6,333,398 B1 | 12/2001 | Blank |
| 6,339,142 B1 | 1/2002 | Basey et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,417,335 B1 | 7/2002 | Basey et al. |
| 6,441,163 B1 | 8/2002 | Chari et al. |
| 6,489,447 B1 | 12/2002 | Basey et al. |
| 6,573,043 B1 | 6/2003 | Cohen et al. |
| 6,627,196 B1 | 9/2003 | Baughman et al. |
| 6,632,979 B2 | 10/2003 | Erickson et al. |
| 6,639,055 B1 | 10/2003 | Carter et al. |
| 6,685,940 B2 | 2/2004 | Andya et al. |
| 6,719,971 B1 | 4/2004 | Carter et al. |
| 6,797,814 B2 | 9/2004 | Blank |
| 6,800,738 B1 | 10/2004 | Carter et al. |
| 6,821,515 B1 | 11/2004 | Cleland et al. |

(Continued)

FOREIGN PATENT DOCUMENTS

| | | |
|---|---|---|
| JP | 2014-502596 A | 2/2014 |
| WO | WO 2012/078771 A1 | 6/2012 |

OTHER PUBLICATIONS

Swain et al. ("Swain", The Lancet, Oncolody, 2013, 14, 461-471). (Year: 2013).*

(Continued)

*Primary Examiner* — Lei Yao

(74) *Attorney, Agent, or Firm* — Baker Botts L.L.P.

(57) ABSTRACT

Methods of treating patients having HER2-positive, locally advanced or previously untreated metastatic breast cancer having received prior treatment with a taxane using an anti-HER2-maytansinoid conjugate (for example trastuzumab emtansine) are provided.

20 Claims, 9 Drawing Sheets

Specification includes a Sequence Listing.

(56) References Cited

U.S. PATENT DOCUMENTS

| | | |
|---|---|---|
| 6,905,830 B2 | 6/2005 | Cohen et al. |
| 6,949,245 B1 | 9/2005 | Sliwkowski |
| 6,984,494 B2 | 1/2006 | Ralph |
| 7,018,809 B1 | 3/2006 | Carter |
| 7,041,292 B1 | 5/2006 | Sliwkowski |
| 7,060,268 B2 | 6/2006 | Andya et al. |
| 7,074,404 B2 | 7/2006 | Basey et al. |
| 7,097,840 B2 | 8/2006 | Erickson et al. |
| 7,129,051 B2 | 10/2006 | Cohen et al. |
| 7,279,287 B2 | 10/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 2/2009 | Adams et al. |
| 7,485,704 B2 | 2/2009 | Fahrner et al. |
| 7,498,030 B2 | 3/2009 | Adams et al. |
| 7,501,122 B2 | 3/2009 | Adams et al. |
| 7,531,645 B2 | 5/2009 | Basey et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,618,631 B2 | 11/2009 | Sliwkowski |
| 7,674,589 B2 | 3/2010 | Cohen et al. |
| 7,682,609 B2 | 3/2010 | Andya et al. |
| 7,700,299 B2 | 4/2010 | Moecks et al. |
| 7,807,799 B2 | 10/2010 | Fahrner et al. |
| 7,811,773 B2 | 10/2010 | Ralph |
| 7,846,441 B1 | 12/2010 | Hellmann |
| 7,850,966 B2 | 12/2010 | Lowman et al. |
| 7,862,817 B2 | 1/2011 | Adams et al. |
| 7,879,325 B2 | 2/2011 | Kao et al. |
| 7,892,549 B2 | 2/2011 | Paton et al. |
| 7,919,254 B2 | 4/2011 | Cohen et al. |
| 7,981,418 B2 | 7/2011 | Amler et al. |
| 7,993,834 B2 | 8/2011 | Mass |
| 8,044,017 B2 | 10/2011 | Emery et al. |
| 8,075,890 B2 | 12/2011 | Carter et al. |
| 8,075,892 B2 | 12/2011 | Hellmann |
| 8,076,066 B2 | 12/2011 | Mass |
| 8,142,784 B2 | 3/2012 | Ebens, Jr. et al. |
| 8,163,287 B2 | 4/2012 | Sliwkowski |
| 8,241,630 B2 | 8/2012 | Kao et al. |
| 8,247,397 B2 | 8/2012 | Belvin et al. |
| 2001/0014326 A1 | 8/2001 | Andya et al. |
| 2002/0001587 A1 | 1/2002 | Erickson et al. |
| 2002/0035736 A1 | 3/2002 | Erickson et al. |
| 2002/0090662 A1 | 7/2002 | Ralph |
| 2003/0147884 A1 | 8/2003 | Paton et al. |
| 2003/0152987 A1 | 8/2003 | Cohen et al. |
| 2003/0202972 A1 | 10/2003 | Andya et al. |
| 2004/0037823 A9 | 2/2004 | Paton et al. |
| 2004/0082047 A1 | 4/2004 | Emery et al. |
| 2004/0106161 A1 | 6/2004 | Bossenmaier et al. |
| 2004/0258685 A1 | 12/2004 | Brunetta et al. |
| 2005/0002928 A1 | 1/2005 | Hellmann |
| 2005/0063972 A1 | 3/2005 | Basey et al. |
| 2005/0100944 A1 | 5/2005 | Cohen et al. |
| 2005/0166993 A1 | 8/2005 | Viken et al. |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2005/0244929 A1 | 11/2005 | Carter |
| 2005/0276812 A1 | 12/2005 | Ebens, Jr. et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0046270 A1 | 3/2006 | Ralph |
| 2006/0067930 A1 | 3/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |
| 2006/0099201 A1 | 5/2006 | Andya et al. |
| 2006/0121044 A1 | 6/2006 | Amler et al. |
| 2006/0165702 A1 | 7/2006 | Allison et al. |
| 2006/0182739 A1 | 8/2006 | Basey et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0275305 A1 | 12/2006 | Bryant |
| 2007/0009976 A1 | 1/2007 | Lenz et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0166753 A1 | 7/2007 | Mass |
| 2007/0184055 A1 | 8/2007 | Sliwkowski |
| 2007/0224203 A1 | 9/2007 | Friess et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0050748 A1 | 2/2008 | Cohen et al. |
| 2008/0102069 A1 | 5/2008 | Friess et al. |
| 2008/0108096 A1 | 5/2008 | Ralph |
| 2008/0112958 A1 | 5/2008 | Mass |
| 2008/0160026 A1 | 7/2008 | Ashkenazi et al. |
| 2008/0171040 A1 | 7/2008 | Ebens et al. |
| 2008/0187533 A1 | 8/2008 | Hellmann |
| 2008/0226659 A1 | 9/2008 | Erickson |
| 2008/0241146 A1 | 10/2008 | Ashkenazi et al. |
| 2008/0286280 A1 | 11/2008 | Kallmeyer et al. |
| 2008/0317753 A1 | 12/2008 | Amler et al. |
| 2009/0081223 A1 | 3/2009 | Allison et al. |
| 2009/0087432 A1 | 4/2009 | Sliwkowski |
| 2009/0098135 A1 | 4/2009 | Belvin et al. |
| 2009/0099344 A1 | 4/2009 | Fahrner et al. |
| 2009/0148402 A1 | 6/2009 | Brunetta et al. |
| 2009/0148435 A1 | 6/2009 | Lebreton et al. |
| 2009/0155259 A1 | 6/2009 | Derynck et al. |
| 2009/0155803 A1 | 6/2009 | Cohen et al. |
| 2009/0187007 A1 | 7/2009 | Lowman et al. |
| 2009/0202536 A1 | 8/2009 | Ebens, Jr. et al. |
| 2009/0202546 A1 | 8/2009 | Harris et al. |
| 2009/0220492 A1 | 9/2009 | Basey et al. |
| 2009/0226455 A1 | 9/2009 | Filvaroff |
| 2009/0239236 A1 | 9/2009 | Mass |
| 2009/0285837 A1 | 11/2009 | Kao et al. |
| 2009/0317387 A1 | 12/2009 | Paton et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0112603 A1 | 5/2010 | Moecks et al. |
| 2010/0120053 A1 | 5/2010 | Cohen et al. |
| 2010/0158899 A1 | 6/2010 | Andya et al. |
| 2010/0285010 A1 | 11/2010 | Friess et al. |
| 2010/0298156 A1 | 11/2010 | Lee-hoeflich et al. |
| 2011/0027190 A1 | 2/2011 | Hasmann et al. |
| 2011/0033460 A1 | 2/2011 | Fendly et al. |
| 2011/0044977 A1 | 2/2011 | Adler et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0129464 A1 | 6/2011 | Adams et al. |
| 2011/0151454 A1 | 6/2011 | Lee-hoeflich et al. |
| 2011/0159014 A1 | 6/2011 | Lowman et al. |
| 2011/0165155 A1 | 7/2011 | Agresta et al. |
| 2011/0165157 A1 | 7/2011 | Derynck et al. |
| 2011/0223159 A1 | 9/2011 | Friess et al. |
| 2011/0223619 A1 | 9/2011 | Belvin et al. |
| 2011/0236383 A1 | 9/2011 | Andya et al. |
| 2011/0245103 A1 | 10/2011 | Amler et al. |
| 2011/0246399 A1 | 10/2011 | Amler et al. |
| 2011/0250194 A1 | 10/2011 | Hellmann |
| 2012/0003217 A1 | 1/2012 | Bryant |
| 2012/0034213 A1 | 2/2012 | Hellmann |

(56) References Cited

U.S. PATENT DOCUMENTS

| | | | |
|---|---|---|---|
| 2012/0034609 | A1 | 2/2012 | Mass |
| 2012/0065381 | A1 | 3/2012 | Emery et al. |
| 2012/0093838 | A1 | 4/2012 | Mass |
| 2012/0107302 | A1 | 5/2012 | Berry et al. |
| 2012/0107391 | A1 | 5/2012 | Kelsey |
| 2012/0121586 | A1 | 5/2012 | Kiermaier et al. |

OTHER PUBLICATIONS

Welslau et al. ("Welslau", Cancer, 2014, 120, 642-651, published online Nov. 12, 2013) (Year: 2013).*
Hurvitz et al. ("Hurvitz", J. Clin. Onc., 2013, 31, 1157-1163) (Year: 2013).*
Boyarz et al. ("Boyraz", Surr. Med. Res & Opinion, 2013, 29, 405-414) (Year: 2013).*
Horiguchi et al. ("Horiguchi" Anticancer Res., 2009, 29, 517-524). (Year: 2009).*
Clinical trial NCT01276041 (first posted Jan. 2011) (Year: 2011).*
Verma et al, NEJM, 367:1783-1791, 2012 (Year: 2012).*
Clinical trial NCT-00829166, first posted Feb. 2009, results first posted Apr. 2013 (Year: 2013).*
Baselga et al, NEJM, 366:109-19, Jan. 2012 (Year: 2012).*
Clinical trial NCT01120184 (first posted May 10, 2010 (Year: 2010).*
Agus et al., "Clinical activity in a phase I trial of HER-2-targeted rhuMAB 2C4 (pertuzumab) in patients with advanced solid malignancies (AST)," Proceedings of ASCO 22:192 (2003).
Agus et al., "Targeting ligand-activated ErbB2 signaling inhibit breast and prostate tumor growth," Cancer Cell 2:127-137 (2002).
Allison et al., "Pharmacokinetics of HER2-targeted rhuMAb 2C4 (pertuzumab) in patients with advanced solid malignancies: Phase Ia results," Pro Am Soc Clin Oncol 22:197 (2003).
Barginear et al., "Trastuzumab-DM1: A Clinical Update of the Novel Antibody-Drug Conjugate for HER2-Overexpressing Breast Cancer," Molecular Medicine, 18:1473-1479 (2012).
Baselga et al., "Objective response rate in a phase II multicenter trial of pertuzumab (P), a HER2 dimerization inhibiting monoclonal antibody, in combination with trastuzumab (T) in patients (pts) with HER2-positive metastatic breast cancer (MBC) which progressed during treatment with T," J Clin Oncol, 2007 ASCO Annual Meeting Proceedings Part I, 25(18S):1004 (2007).
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14:737-744 (1996).
Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts," Cancer Res. 58:2825-2831 (1998).
Beeram et al., "A Phase 1 Study of Weekly Dosing of Trastuzumab Emtansine (T-DM1) in Patients with Advanced Human Epidermal Growth Factor 2-Positive Breast Cancer" Cancer 118:5733-5740 (2012).
Beeram et al., "MM-111—A novel bispecific antibody targeting HER-2/HER-3 heterodimer: Safety and tolerability in a first-in-human Phase I/II study in patients with refractory HER-2-positive (HER-2+) cancers," The Start Center for Cancer Care Poster (2012).
Cabanillas et al., "Results of a Phase II Study of Maytansine in Patients with Breast Carcinoma and Melanoma," Cancer Treat Rep, 63:507-509 (1979).
Cassady et al., "Recent Developments in the Maytansinoid Antitumor Agents," Chem. Pharm Bull 52(1):1-26 (2004).
Cho et al., "Structure of the extracellular region of HER2 alone and in complex with the Herceptin Fab," Nature 421:756-760 (2003).
Coussens et al., "Tyrosine Kinase Receptor with Extensive Homology to EGF Receptor Shares Chromosomal Location with neu Oncogene," Science 230:1132-1139 (1985).
F. Hoffmann-La Roche Ltd. et al., "Roche provides update on Phase III MARIANNE study in people with previously untreated advanced HER2-positive breast cancer," Dec. 19, 2014 https://www.roche.com/investors/updates/inv-update-2014-12-19.htm (Accessed on Oct. 25, 2018).
Finn et al., "Expression of EGFR ligands betacellulin and tenascin C are associated with molecular response following gefitinib treatment in women with primary breast cancer," [Abstract #1043] Breast Cancer Res Treat 100 (Suppl 1):S52 (2006).
Franklin et al., "Insights into ErbB signaling from the structure of the ErbB2-pertuzumab complex," Cancer Cell 5:317-328 (2004).
Girish et al., "Clinical pharmacology of trastuzumab emtansine (T-DM1): an antibody-drug conjugate in development for the treatment of HER2-positive cancer," Cancer Chemotherapy and Pharmacology 69:1229-1240 (2012).
Harari et al., "Molecular mechanisms underlying ErbB2/HER2 action in breast cancer," Oncogene 19:6102-6114 (2000).
Hoffman-La Roche, "A Study of Trastuzumab Emtansine (T-DM1) Plus Pertuzumab/Pertuzumab Placebo Versus Trastuzumab [Herceptin] Plus a Taxane in Participants with Metastatic Breast Cancer (MARIANNE)," Clinical Trials, NCT01120184, May 10, 2010 (Accessed on Oct. 25, 2018).
Hotaling et al., "The humanized anti-HER2 antibody rhuMab HER2 mediates antibody dependant cell-mediated cytotoxicity via FcγR III," [abstract #3215] Proc. 87th Annual Meeting Am Assoc Cancer Res 37:471 (1996).
Hudziak et al., "p185HER2 Monoclonal Antibody Has Antiproliferative Effects In Vitro and Sensitizes Human Breast Tumor Cells to Tumor Necrosis Factor," Mol. Cell Biol. 9(3):1165-1172 (1989).
International Search Report dated Jan. 2, 2017 in International Application No. PCT/US2016/034835.
Issell et al., "Maytansine," Cancer Treat Rev 5:199-207 (1978).
Jemal et al., "Global Cancer Statistics," CA Cancer J Clin, 61:69-90 (2011).
Krop et al., "A Phase II Study of Trastuzumab Emtansine in Patients with Human Epidermal Growth Factor Receptor 2-Positive Metastatic Breast Cancer Who Were Previously Treated with Trastuzumab, Lapatinib, an Anthracycline, a Taxane, and Capecitabine," 30(26):3234-3241 (2012).
Krop et al., "Phase I Study of Trastuzumab-DM1, an HER2 Antibody-Drug Conjugate, Given Every 3 Weeks to Patients with HER2-Positive Metastatic Breast Cancer," J. Clin. Oncol. 28(16):2698-2704 (2010).
Lewis et al., "Differential responses of human tumor cell lines to anti-p185HER2 monoclonal antibodies," Cancer Immunol Immunother 37:255-263 (1993).
Lewis Phillips et al., "Targeting HER2-Positive Breast Cancer with Trastuzumab-DM1, an Antibody-Cytotoxic Drug Conjugate," Cancer Research, 68(22):9280-9290 (2008).
Malik et al., "Dose-Response Studies of Recombinant Humanized Monoclonal Antibody 2C4 in Tumor Xenograft Models," [abstract] Proceedings of the AACR, vol. 44 (2003).
Marty et al., "Randomized Phase II Trial of the Efficacy and Safety of Trastuzumab Combined with Docetaxel in Patients with Human Epidermal Growth Factor Receptor 2-Positive Metastatic Breast Cancer Administered as First-Line Treatment: The M77001 Study Group," J Clin Oncol 23:4265-4274 (2005).
Miller et al., "Phase IIa Trial of Trastuzumab Emtansine With Pertuzumab for Patients with Human Epidermal Growth Factor Receptor 2-Positive, Locally Advanced, or Metastatic Breast Cancer," Journal of Clinical Oncology, 32(14):1437-1444 (2014).
Nicolaou et al., "Calicheamicin $\theta^1$ 1: A Rationally Designed Molecule with Extremely Potent and Selective DNA Cleaving Properties and Apoptosis Inducing Activity," Angew Chem. Int. Ed. Engl. 33(2):183-186 (1994).
Pegram et al., "Antibody dependent cell-mediated cytotoxicity in breast cancer patients in Phase III clinical trials of a humanized anti-HER2 antibody," [abstract #4044] Proc 88th Annual Meeting Am Assoc Cancer Res 38:602 (1997).
Phillips et al., "Dual Targeting of HER2-Positive Cancer with Trastuzumab Emtansine and Pertuzumab: Critical Role for Neuregulin Blockade in Antitumor Response to Combination Therapy," Clinical Cancer Research, 20(2):456-468 (2013).

(56) References Cited

OTHER PUBLICATIONS

Piccart-Gebhart et al., "Trastuzumab after Adjuvant Chemotherapy in HER2-Positive Breast Cancer," N Engl J Med 353(16):1659-1672 (2005).

Pillow et al., "Site-Specific Trastuzumab Maytansinoid Antibody-Drug Conjugates with Improved Therapeutic Activity through Linker and Antibody Engineering," Journal of Medicinal Chemistry, 57:7890-7899 (2014).

Portera et al., "A report of cardiac events in a phase II clinical study using trastuzumab combined with pertuzumab in HER2-positive metastatic breast cancer (MBC)," J Clin Oncol, 2007 ASCO Annual Meeting Proceedings, 25(18S):39S (2007).

Press et al., "Her-2/neu Expression in Node-negative Breast Cancer: Direct Tissue Quantitation by Computerized Image Analysis and Association of Overexpression with Increased Risk of Recurrent Disease," Cancer Res 53:4960-4970 (1993).

Remillard et al., "Antimitotic Activity of the Potent Tumor Inhibitor Maytansine," Science 189:1002-1005 (1975).

Romond et al., "Trastuzumab plus Adjuvant Chemotherapy for Operable HER2-Positive Breast Cancer," N Engl J Med 353(16):1673-1684 (2005).

Slamon et al., "Human Breast Cancer: Correlation of Relapse and Survival with Amplification of the HER-2/neu Oncogene," Science 235:177-182 (1987).

Slamon et al., "Studies of the HER-2/neu Proto-oncogene in Human Breast and Ovarian Cancer," Science 244:707-712 (1989).

Slamon et al., "Use of Chemotherapy Plus a Monoclonal Antibody Against Her2 for Metastatic Breast Cancer That Overexpresses Her2," N Engl. J. Med 344(11):783-792 (2001).

Sliwkowski et al., "Nonclinical Studies Addressing the Mechanism of Action of Trastuzumab (Herceptin)," Seminars in Oncology 26(4), Suppl 12:60-70 (1999).

Sliwkowski, "Ready to partner," Nat Struct Biol. 10(3):158-159 (2003).

Verma et al., "Trastuzumab Emtansine for HER2-Positive Advanced Breast Cancer," New England Journal of Medicine 367(19):1783-1791 (2012).

Vogel et al., "Efficacy and Safety of Trastuzumab as a Single Agent in First-Line Treatment of HER2-Overexpressing Metastatic Breast Cancer," J Clin Oncol 20:719-726 (2002).

Yarden et al., "Untangling the ErbB Signalling Network," Nat Rev Mol Cell Biol 2:127-137 (2001).

\* cited by examiner

Variable Light

```
              10         20          30         40
2C4     DIVMTQSHKIMSTSVGDRVSITC [RASQDVSIGVA] WYQQRP
        **    **** *              *                *
574     DIQMTQSPSSLSASVGDRVTITC [KASQDVSIGVA] WYQQKP
                                 *   * hum kI  DIQMTQSPSSLSASVGDRVTITC [RASQSISNYLA] WYQQKP 50         60          0          80
2C4     GQSPKLLIY [SASYRYT] GVPDRFTGSGSGTDFTFTISSVQA
        **                      * *           *   **
574     GKAPKLLIY [SASYRYT] GVPSRFSGSGSGTDFTLTISSLQP
                  * ***** hum kI  GKAPKLLIY [AASSLES] GVPSRFSGSGSGTDFTLTISSLQP 90        100
2C4     EDLAVYYC [QQYYIYPYT] FGGGTKLEIK (SEQ ID NO:5)
         *                  *   *
574     EDFATYYC [QQYYIYPYT] FGQGTKVEIK (SEQ ID NO:7)
                 ***  * hum kI  EDFATYYC [QQYNSLPWT] FGQGTKVEIK (SEQ ID NO:9)
```

FIG. 2A

Variable Heavy

```
              10         20            30          40
2C4     EVQIQQSGPELVKPGTSVKISCKAS [GFTFTDYTMD] WVKQS
         **   **  *     *** *                     * *
574     EVQLVESGGGLVQPGGSLRLSCAAS [GFTFTDYTMD] WVRQA
                                    ** * * hum III EVQLVESGGGLVQPGGSLRLSCAAS [GFTFSSYAMS] WVRQA 50    a      60             70          80
2C4     HGKSLEWIG [DVNPNSGGSIYNQRFKG] KASLTVDRSSRIVYM
         *   * **                     *** *    **** *
574     PGKGLEWVA [DVNPNSGGSIYNQRFKG] RFTLSVDRSKNTLYL
                  **** * ****             * * hum III PGKGLEWVA [VISGDGGSTYYADSVKG] RFTISRDNSKNTLYL abc    90       100ab         110
2C4     ELRSLTFEDTAVYYCAR [NLGPSFYFDY] WGQGTTLTVSS (SEQ ID NO:6)
        *** **                         **
574     QMNSLRAEDTAVYYCAR [NLGPSFYFDY] WGQGTLVTVSS (SEQ ID NO:8)
                           ******** hum III QMNSLRAEDTAVYYCAR [SRVGYSLYDY] WGQGTLVTVSS (SEQ ID NO:10)
```

FIG. 2B

Amino Acid Sequence for Pertuzumab Light Chain

```
  1         10         20         30         40         50         60
  |         |          |          |          |          |          |
DIQMTQSPSSLSASVGDRVTITCKASQDVSIGVAWYQQKPGKAPKLLIYSASYRYTGVPS 70         80         90        100        110        120
          |          |          |          |          |          |
RFSGSGSGTDFTLTISSLQPEDFATYYCQQYYIYPYTFGQGTKVEIKRTVAAPSVFIFPP 130        140        150        160        170        180
          |          |          |          |          |          |
SDEQLKSGTASVVCLLNNFYPREAKVQWKVDNALQSGNSQESVTEQDSKDSTYSLSSTLT 190        200        210
          |          |          |
LSKADYEKHKVYACEVTHQGLSSPVTKSFNRGEC  (SEQ ID NO: 11)
```

*FIG. 3A*

Amino Acid Sequence for Pertuzumab Heavy Chain

```
  1         10         20         30         40         50         60
  |          |          |          |          |          |          |
EVQLVESGGGLVQPGGSLRLSCAASGFTFTDYTMDWVRQAPGKGLEWVADVNPNSGGSIY 70         80         90        100        110        120
          |          |          |          |          |          |
NQRFKGRFTLSVDRSKNTLYLQMNSLRAEDTAVYYCARNLGPSFYFDYWGQGTLVTVSSA 130        140        150        160        170        180
          |          |          |          |          |          |
STKGPSVFPLAPSSKSTSGGTAALGCLVKDYFPEPVTVSWNSGALTSGVHTFPAVLQSSG 190        200        210        220        230        240
          |          |          |          |          |          |
LYSLSSVVTVPSSSLGTQTYICNVNHKPSNTKVDKKVEPKSCDKTHTCPPCPAPELLGGP 250        260        270        280        290        300
          |          |          |          |          |          *|
SVFLFPPKPKDTLMISRTPEVTCVVVDVSHEDPEVKFNWYVDGVEVHNAKTKPREEQYNS 310        320        330        340        350        360
          |          |          |          |          |          |
TYRVVSVLTVLHQDWLNGKEYKCKVSNKALPAPIEKTISKAKGQPREPQVYTLPPSREEM 370        380        390        400        410        420
          |          |          |          |          |          |
TKNQVSLTCLVKGFYPSDIAVEWESNGQPENNYKTTPPVLDSDGSFFLYSKLTVDKSRWQ 430        440        448
          |          |          |
QGNVFSCSVMHEALHNHYTQKSLSLSPG  (SEQ ID NO: 12)
```

*FIG. 3B*

Trastuzmab Light Chain

```
1                           15                          30                          45
DIQMTQSPSSLSASVGDRVTITCRASQDVNTAVAWYQQKPGKAPK
46                          60                          75                          90
LLIYSASFLYSGVPSRFSGSRSGTDFTLTISSLQPEDFATYYCQQ
91                          105                         120                         135
HYTTPPTFGQGTKVEIKRTVAAPSVFIFPPSDEQLKSGTASVVCL
136                         150                         165                         180
LNNFYPREAKVQWKVDNALQSGNSQESVTEQDSKDSTYSLSSTLT
181                         195                         210    214
LSKADYEKHKVYACEVTHQGLSSPVTKSFNRGEC    (SEQ ID NO: 13)
```

FIG. 4A

Trastuzumab Heavy Chain

```
1   EVQLVESGGG LVQPGGSLRL SCAASGFNIK DTYIHWVRQA PGKGL      45
46  EWVARIYPTN GYTRYADSVK GRFTISADTS KNTAYLQMNS LRAED      90
91  TAVYYCSRWG GDGFYAMDYW GQGTLVTVSS ASTKGPSVFP LAPSS      135
136 KSTSGGTAAL GCLVKDYFPE PVTVSWNSGA LTSGVHTFPA VLQSS      180
181 GLYSLSSVVT VPSSSLGTQT YICNVNHKPS NTKVDKKVEP KSCDK      225
226 THTCPPCPAP ELLGGPSVFL FPPKPKDTLM ISRTPEVTCV VVDVS      270
271 HEDPEVKFNW YVDGVEVHNA KTKPREEQYN STYRVVSVLT VLHQD      315
316 WLNGKEYKCK VSNKALPAPI EKTISKAKGQ PREPQVYTLP PSREE       360
361 MTKNQVSLTC LVKGFYPSDI AVEWESNGQP ENNYKTTPPV LDSDG      405
406 SFFLYSKLTV DKSRWQQGNV FSCSVMHEAL HNHYTQKSLS LSPG       449
```

(SEQ ID NO: 14)

*FIG. 4B*

Pertuzumab Variant Light Chain

```
  1 D I Q M T Q S P S S L S A S V G D R V T I T C K A S Q D V S I G V A W Y Q Q K P G K
 46 A P K L L I Y S A S Y R Y T G V P S R F S G S G S G T D F T L T I S S L Q P E D F A T Y Y
 91 C Q Q Y Y I Y P Y T F G Q G T K V E I K R T V A A P S V F I F P P S D E Q L K S G T A S V
136 V C L L N N F Y P R E A K V Q W K V D N A L Q S G N S Q E S V T E Q D S K D S T Y S L S S
181 T L T L S K A D Y E K H K V Y A C E V T H Q G L S S P V T K S F N R G E C    (SEQ ID NO: 15)
```

*FIG. 5A*

Pertuzumab Variant Heavy Chain

```
1   E V Q L V E S G G G L V Q P G G S L R L S C A A S G F T F T D Y T M D W V R Q A P G K G L   45
46  E W V A D V N P N S G G S I N Q R F K G R F T L S V D R S K N T L Y L Q M N S L R A E D    90
91  T A V Y Y C A R N L G P S F Y F D Y W G Q G T L V T V S S A S T K G P S V F P L A P S S K  135
136 S T S G G T A A L G C L V K D Y F P E P V T V S W N S G A L T S G V H T F P A V L Q S S G  180
181 L Y S L S S V V T V P S S S L G T Q T Y I C N V N H K P S N T K V D K K V E P K S C D K T  225
226 H T C P P C P A P E L L G G P S V F L F P P K P K D T L M I S R T P E V T C V V V D V S H  270
271 E D P E V K F N W Y V D G V E V H N A K T K P R E E Q Y N S T Y R V V S V L T V L H Q D W  315
316 L N G K E Y K C K V S N K A L P A P I E K T I S K A K G Q P R E P Q V Y T L P P S R E E M  360
361 T K N Q V S L T C L V K G F Y P S D I A V E W E S N G Q P E N N Y K T T P P V L D S D G S  405
406 F F L Y S K L T V D K S R W Q Q G N V F S C S V M H E A L H N H Y T Q K S L S L S P G K    449
```

(SEQ ID NO: 16)

FIG. 5B

METHODS OF TREATING HER2-POSITIVE METASTATIC BREAST CANCER

RELATED APPLICATIONS

This application is a national stage entry application filed under 35 USC § 371 of PCT Application No. PCT/US2016/034835, filed May 27, 2016, which claims benefit of priority under 35 USC § 119(e) of provisional application No. 62/168,809, filed May 30, 2015, the entire disclosures of which are hereby incorporated by reference in their entirety.

SEQUENCE LISTING

The instant application contains a Sequence Listing in ASCII format and is hereby incorporated by reference in its entirety. The ASCII text file was created on May 20, 2016, is named GNE-0423R1-WO Sequence Listing.txt and is 30,476 bytes in size.

FIELD OF THE INVENTION

The invention relates to methods of using anti-HER2-maytansinoid conjugates, such as trastuzumab-MCC-DM1, for the treatment of HER2-positive progressive or recurrent locally advanced or previously untreated metastatic breast cancer, where the patient has received prior treatment with a taxane.

BACKGROUND OF THE INVENTION

Breast Cancer and HER2 Targeted Treatments

Breast cancer is a highly significant cause of morbidity and mortality worldwide There are over 1.3 million cases of breast cancer diagnosed globally each year with more than 450,000 deaths related to the disease (Jemal A. Bray F. Center M. et al. Global cancer statistics. CA Cancer J Clin, 2011: 61(2):69-90).

The HER2 (ErbB2) receptor tyrosine kinase is a member of the epidermal growth factor receptor (EGFR) family of transmembrane receptors. Overexpression of HER2 is observed in approximately 20% of human breast cancers (hereinafter referred to as HER2-positive breast cancer) and is implicated in the aggressive growth and poor clinical outcomes associated with these tumors (Slamon et al (1987) Science 235:177-182). HER2 protein overexpression can be determined using an immunohistochemistry based assessment of fixed tumor blocks (Press M F. et al (1993) Cancer Res 53:4960-70).

Trastuzumab (CAS 180288-69-1, HERCEPTIN®, huMAb4D5-8, rhuMAb HER2. Genentech) is a recombinant DNA-derived, IgG1 kappa, monoclonal antibody that is a humanized version of a murine anti-HER2 antibody (4D5) that selectively binds with high affinity in a cell-based assay (Kd 5 nM) to the extracellular domain of HER2 (U.S. Pat. No. 5,677,171: U.S. Pat. No. 5,821,337: U.S. Pat. No. 6,054,297: U.S. Pat. No. 6,165,464: U.S. Pat. No. 6,339,142: U.S. Pat. No. 6,407,213: U.S. Pat. No. 6,639,055: U.S. Pat. No. 6,719,971: U.S. Pat. No. 6,800,738: U.S. Pat. No. 7,074,404: Coussens et al (1985) Science 230:1132-9: Slamon et al (1980) Science 244:707-12: Slamon et al (2001) New Engl. J. Med, 344:783-792). Trastuzumab has been shown, in both in vitro assays and in animals, to inhibit the proliferation of human tumor cells that overexpress HER2 (Hudziak et al (1989) Mol Cell Biol 9:1165-72: Lewis et al (1993) Cancer Immunol Immunother; 37:255-63: Baselga et al (1998) Cancer Res. 58:2825-2831). Trastuzumab is a mediator of antibody-dependent cellular cytotoxicity. ADCC (Lewis et al (1993) Cancer Immunol Immunother 37(4):255-263: Hotaling et al (1996) [abstract]. Proc. Annual Meeting Am Assoc Cancer Res: 37:471: Pegram M D et al (1997) [abstract]. Proc Am Assoc Cancer Res: 38:601 Sliwkowski et al (1999) Seminars in Oncology 26(4), Suppl 12:60-70: Yarden Y. and Sliwkowski, M. (2001) Nature Reviews: Molecular Cell Biology, Macmillan Magazines, Ltd., Vol. 2:127-137).

HERCEPTIN® was approved in 1998 for the treatment of patients with HER2-overexpressing metastatic breast cancers (Baselga et al. (1996) J. Clin. Oncol. 14:737-744) that have received extensive prior anti-cancer therapy, and has since been used in over 300,000 patients (Slamon D J, et al. N End J Med 2001:344:783 92: Vogel C L, et al. J Clin Oncol 2002:20:719 26: Marty M. et al. J Clin Oncol 2005: 23:4265 74: Romond E H, et al. T N Engl J Med 2005:353: 1673-84: Piccart-Gebhart M J, et al. N Engl J Med 2005: 353:1650-72: Slamon D, et al. [abstract]. Breast Cancer Res Treat 2006, 100 (Suppl 1): 52). In 2006, the FDA approved HERCEPTIN® (trastuzumab, Genentech Inc.) as part of a treatment regimen containing doxorubicin, cyclophosphamide and paclitaxel for the adjuvant treatment of patients with HER2-positive, node-positive breast cancer.

An alternative approach to antibody-targeted therapy is to utilize antibodies for delivery of cytotoxic drugs specifically to antigen-expressing cancer cells. Antibody-drug conjugates, or ADCs, are monoclonal antibodies to which highly potent cytotoxic agents have been conjugated. ADCs represent a novel approach to conferring tumor selectivity on systemically administered anti-tumor therapeutics. Utilising surface antigens that are tumor-specific and/or overexpressed. ADCs are designed to focus the delivery of highly potent cytotoxic agents to tumor cells. The potential of this approach is to create a more favorable therapeutic window for such agents than could be achieved by their administration as free drugs.

Maytansinoids, derivatives of the anti-mitotic drug maytansine, bind to microtubules in a manner similar to vinca alkaloid drugs (Issell B F et al (1978) Cancer Treat. Rev 5:199-207; Cabanillas F et al. (1079) Cancer Treat Rep. 63:507 9. DM1 is a thiol-containing maytansinoid derived from the naturally occurring ester ansamitocin P3 (Remillard S. Rebhan I. I, Howie G A. et al. (1975) Science 189(4207):1002 1005.3: Cassady J M, Chan K K, Floss H G. (2004) Chem Pharm Bull 52(1);1 26.4). The related plant ester, maytansine, has been studied as a chemotherapeutic agent in approximately 800 patients, administered at a dose of 2.0 mg/m2 every 3 weeks either as a single dose or for 3 consecutive days (Issell B F, Crooke S T. (1978) Maytansine. Cancer Treat Rev 5:199-207). Despite preclinical activity, the activity of maytansine in the clinic was modest at doses that could be safely delivered. The dose-limiting toxicity (DLT) was gastrointestinal, consisting of nausea, vomiting, and diarrhea (often followed by constipation). These toxicities were dose dependent but not schedule dependent. Peripheral neuropathy (predominantly sensory) was reported and was most apparent in patients with pre-existing neuropathy. Subclinical transient elevations of hepatic transaminase, alkaline phosphatase, and total bilirubin were reported. Constitutional toxicities, including weakness, lethargy, dysphoria, and insomnia, were common. Less common toxicities included infusion-site phlebitis and mild myelosuppression. Further development of the drug was abandoned in the 1980s because of the narrow therapeutic window.

Trastuzumab-MCC-DM1 (T-DM1 trastuzumab emtansine, ado-trastuzumab emtansine, KADCYLA®), a novel antibody-drug conjugate (ADC) for the treatment of HER2-positive breast cancer, is composed of the cytotoxic agent DM1 (a thiol-containing maytansinoid anti-microtubule agent) conjugated to trastuzumab at lysine side chains via an MCC linker, with an average drug load (drug to antibody ratio) of about 3.5. After binding to HER2 expressed on tumor cells, T-DM1 undergoes receptor-mediated internalization, resulting in intracellular release of cytotoxic catabolites containing DM1 and subsequent cell death.

In a Phase 1 study of T-DM1 (TDM3569g), the maximum tolerated dose (MTD) of T-DM1 administered by IV infusion every 3 weeks (q3w) was 3.6 mg/kg. A DLT (Dose-Limiting Toxicity) consisted of transient thrombocytopenia in patients treated at 4.8 mg/kg. Treatment with 3.6 mg/kg was well tolerated and associated with significant clinical activity. (Krop (2010) J. Clin. Oncol. 28(16):2698-2704). That same study also showed that weekly dosing with 2.4 mg/kg was also well tolerated and had anti-tumor activity. (Beeram (2012) Cancer 118(23):5733-5740.)

A Phase II study (TDM4374g) demonstrated that T-DM1, administered at 3.6 mg/kg q3w, had single-agent anti-tumor activity in a heavily pre-treated patient population having HER2-positive metastatic breast cancer. (Krop (2012) 30(26):3234-3241.) A Phase III study (TDM4370g, "EMILIA") demonstrated that T-DM1, administered at 3.6 mg/kg q3w, significantly prolonged progression-free survival and overall survival with less toxicity compared to treatment with lapatinib plus capecitabine in patients with HER2-positive advanced breast cancer ($2^{nd}$ and $3^{rd}$ line metastatic breast cancer) previously treated with trastuzumab and a taxane. (Verma (2012) New England Journal of Medicine 367:1783-1791.)

The U.S. Food and Drug Administration approved ado-trastuzumab emtansine, marketed under the tradename KADCYLA®, on Feb. 22, 2013 for the treatment of patients with HER2-positive, metastatic breast cancer who previously received treatment with trastuzumab and a taxane.

Pertuzumab (also known as recombinant humanited monoclonal antibody 2C4, rhuMAb 2C4, PERJETA®, Genentech, Inc, South San Francisco) represents the first in a new class of agents known as HER dimerization inhibitors (HDI) and functions to inhibit the ability of HER2 to form active heterodimers or homodimers with other HER receptors (such as EGFR/HER1, HER2, HER3 and HER4). See, for example, Harari and Yarden Oncogene 19:6102-14 (2000): Yarden and Sliwkowski. Nat Rev Mol Cell Biol 2:127-37 (2001): Sliwkowski Nat Struct Biol 10,158-9 (2003): Cho et al. Nature 421:756-60 (2003): and Malik et al. Pro Am Soc Cancer Res 44:176-7 (2003)

Pertuzumab blockade of the formation of HER2-HER 3 heterodimers in tumor cells has been demonstrated to inhibit critical cell signaling, which results in reduced tumor proliferation and survival (Agus et al. Cancer Cell 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable locally advanced, recurrent or metastatic solid tumors that had progressed during or after standard therapy were treated with pertuzumab given intravenously every 3 weeks. Pertuzumab was generally well tolerated. Tumor regression was achieved in 3 of 20 patients evaluable for response. Two patients had confirmed partial responses. Stable disease lasting for more than 2.5 months was observed in 6 of 21 patients (Anus et al, Pro Am Soc Clin Oncol 22:192 (2003)). At doses of 2.0-15 mg/kg, the pharmacokinetics of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. Pro Am Soc Clin Oncol 22:197 (2003)).

US 2006/0034842 describes methods for treating ErbB-expressing cancer with anti-ErbB2 antibody combinations. US 2008/0102069 describes the use of Trastuzumab and Pertuzumab in the treatment of HER2-positive metastatic cancer, such as breast cancer. Baselga et al., J Clin Oncol. 2007 ASCO Annual Meeting Proceedings Part 1. Col. 25. No. 18S (June 20 Supplement). 2007:1004 report the treatment of patients with pre-treated HER2-positive breast cancer, which has progressed during treatment with Trastuzumab, with a combination of Trastuzumab and Pertuzumab. Portera et al. J Clin Oncof 2007 ASCO Annual Meeting Proceedings Part 1. Vol. 25, No. 18S (June 20 Supplement). 2007:1028 evaluated the efficacy and safety of Trastuzumab+Pertuzumab combination therapy in HER2-positive breast cancer patients, who had progressive disease on Trastuzumab-based therapy. The authors concluded that further evaluation of the efficacy of combination treatment was required to define the overall risk and benefit of this treatment regimen.

Pertuzumab has been evaluated in Phase II studies in combination with Trastuzumab in patients with HER2-positive metastatic breast cancer who have previously received Trastuzumab for metastatic disease. One study conducted by the National cancer Institute (NCI), enrolled 11 patients with previously treated HER2-positive metastatic breast cancer. Two out of the 11 patients exhibited a partial response (PR) (Baselga et al. J Clin Oncol 2007 ASCO Annual Meeting Proceedings: 25:18 S (June 20 Supplement): 1004. The results of a Phase II neoadjuvant study evaluating the effect of a novel combination regimen of Pertuzumab and Trastuzumab plus chemotherapy (Docetaxel) in women with early-stage HER2-positive breast cancer, presented at the CTRC-AACR San Antonio Breast Cancer Symposium (SABCS). Dec. 8-12, 2010, showed that the two HER2 antibodies plus Docetaxel given in the neoadjuvant setting prior to surgery significantly improved the rate of complete tumor disappearance (pathological complete response rate, pCR, of 45.8 percent) in the breast by more than half compared to Trastuzumab plus Docetaxel (pCR of 29. 0 percent). p=0.014.

Pertuzumab, marketed under the tradename PERJETAR®, was approved in 2012 for the treatment or patients with advanced or late-stage (metastatic) HER2-positive breast cancer. HER2-positive breast cancers have increased amounts of the HER2 protein that contributes to cancer cell growth and survival.

On Sep. 30, 2013, the U.S. Food and Drug Administration granted accelerated approval to PERJETA® (pertuzumab) as part or a complete treatment regimen for patients with early stage breast cancer (EBC) before surgery (neoadjuvant setting). PERJETA® is the first FDA-approved drug for the neoadjuvant treatment of breast cancer.

Patent Publications related to HER2 antibodies include: U.S. Pat. Nos. 5,677,171: 5,720,937: 5,720,954: 5,725,856: 5,770,195: 5,772,997: 6,165,464: 6,387,371: 6,399,063: 6,015,567: 6,333,169: 4,968,603: 5,821,337: 6,054,297: 6,407,213: 6,639,055: 6,719,971: 6,800,738: 8,075,800: 5,648,237: 7,018,800: 6,267,058: 6,685,940: 6,821,515: 7,060,268: 7,682,609: 7,371,376: 6,127,526: 6,333,398: 6,797,814: 6,339,142: 6,417,335: 6,489,447: 7,074,404:

7,531,645; 7,846,441; 7,892,549; 8,075,802; 6,573,043; 6,905,830; 7,129,051; 7,344,840; 7,468,252; 7,674,589; 7,919,254; 6,949,245; 7,485,302; 7,498,030; 7,501,122; 7,537,931; 7,618,631; 7,862,817; 7,041,292; 6,627,106; 7,371,379; 6,632,979; 7,097,840; 7,575,748; 6,984,494; 7,279,287; 7,811,773; 7,993,834; 8,076,066; 8,044,017; 7,435,797; 7,850,966; 7,485,704; 7,807,799; 8,142,784; 7,560,111; 7,879,325; 8,241,630; 7,449,184; 8,163,287; 7,700,209; 7,081,418; 8,247,307; and US 2010/0016556; US 2005/0244929; US 2001/0014326. US 2003/0202972; US 2006/0099201; US 2010/0158899; US 2011/0236383; US 2011/0033460; US 2008/0286280; US 2005/0063972; US 2006/0182739; US 2000/0220492; US 2003/0147884; US 2004/0037823; US 2005/0002928; US 2007/0292419; US 2008/0187533; US 2011/0250194; US 2012/0034213; US 2003/0152987; US 2005/0100944; US 2006/0183150; US 2008/0050748; US 2000/0155803; US 2010/0120053; US 2005/0244417; US 2007/0026001; US 2008/0160026; US 2008/0241146; US 2005/0208043; US 2005/0238640; US 2006/0034842; US 2006/0073143; US 2006/0193854; US 2006/0108843; US 2011/0129464; US 2007/0184055; US 2007/0269420; US 2008/0050373; US 2006/0083739; US 2009/0087432; US 2006/0210561; US 2002/0035736; US 2002/0001587; US 2008/0226659; US 2002/0090662; US 2006/0046270; US 2008/0108096; US 2007/0166753; US 2008/0112958; US 2000/0239236; US 2012/0034609; US 2012/0093838; US 2004/0082047; US 2012/0065381; US 2009/0187007; US 2011/0150014; US 2004/0106161; US 2011/0117096; US 2004/0258685; US 2009/0148402; US 2009/0099344; US 2006/0034840; US 2011/0064737; US 2005/0276812; US 2008/0171040; US 2009/0202536; US 2006/0013819; US 2012/0107301; US 2006/0018800; US 2000/0285837; US 2011/0117097; US 2006/0088523; US 2010/0015157; US 2006/0121044; US 2008/0317753; US 2006/0165702; US 2009/0081223; US 2006/0188509; US 2000/0155250; US 2011/0165157; US 2006/0204505; US 2006/0212956; US 2006/0275305; US 2012/0003217; US 2007/0009976; US 2007/0020261; US 2007/0037228; US 2010/0112603; US 2006/0067930; US 2007/0224203; US 2011/0064736; US 2008/0038271; US 2008/0050385; US 2010/0285010; US 2011/0223159; US 2008/0102060; US 2010/0008975; US 2011/0245103; US 2011/0246399; US 2011/0027190; US 2010/0208156; US 2011/0151454; US 2011/0223619; US 2012/0107302; US 2009/0008135; US 2009/0148435; US 2009/0202546; US 2009/0226455; US 2000/0317387; US 2011/0044977; US 2012/0121586.

SUMMARY OF THE INVENTION

The invention relates to methods of using anti-HER2-maytansinoid conjugates, such as trastuzumab-MCC-DM1, for the treatment of HER2-positive progressive or recurrent locally advanced or previously untreated metastatic breast cancer (first line metastatic breast cancer), where the patient has been previously treated with a taxane. Although treatment options exist for HER2-positive cancer patients in the adjuvant, neo-adjuvant and metastatic settings. Further options are needed, including in the first line metastatic setting, i.e., for patients with previously untreated metastatic breast cancer, or patients with locally advanced breast cancer.

The present invention is based, in part, on the observation that trastuzumab-MCC-DM1 was unexpectedly effective in treating patients with first line metastatic HER2-positive breast cancer, where the patients had received prior treatment with a taxane, compared with patients who had not received prior taxane.

In one aspect, the instant invention provides methods of treating HER2-positive locally advanced or previously untreated metastatic breast cancer, the method comprising administering to a patient having said breast cancer a therapeutically effective amount of an anti-HER2-maytansinoid conjugate, wherein the patient received prior treatment with a taxane.

In another aspect the instant invention provides use of a therapeutically effective amount of an anti-HER2-maytansinoid conjugate in the manufacture of a medicament for the treatment of HER2-positive locally advanced or previously untreated metastatic breast cancer in a subject, wherein the subject received prior treatment with a taxane.

In certain embodiments, the administration occurs ≥6 months after the prior treatment with a taxane. In some embodiments, the patient received prior treatment with a taxane and at least one HER2-directed therapy. In one embodiment, the patient received prior treatment with a taxane and trastuzumab. In another embodiment, the patient received prior treatment with a taxane, trastuzumab, and pertuzumab. In some embodiments, the prior treatment was administered in the adjuvant setting. In yet other embodiments, the prior treatment was administered in the neoadjuvant setting.

In certain other aspects, the present invention provides methods of treating HER2-positive locally advanced or previously untreated metastatic breast cancer, the methods comprising (1) determining whether a patient has received prior treatment with a taxane, and (2) administering to a patient having said breast cancer a therapeutically effective amount of an anti-HER2-maytansinoid conjugate if the patient has received prior treatment with a taxane. In certain embodiments, the administration occurs ≥6 months after the prior treatment with a taxane. In some embodiments, the patient received prior treatment with taxane and at least one HER2-directed therapy. In one embodiment, the patient received prior treatment with a taxane and trastuzumab. In another embodiment the patient received prior treatment with a taxane, trastuzumab, and pertuzumab. In one embodiment, the prior treatment was administered in the adjuvant setting. In other embodiments, the prior treatment was administered in the neoadjuvant setting.

In certain embodiment of the above aspects, the taxane is paclitaxel. In some embodiments, the paclitaxel was administered at 80 mg/m2 intravenously weekly. In certain embodiments, the paclitaxel was administered for a minimum of 18 weeks.

In other embodiments, the taxane is docetaxel. In some embodiments, the docetaxel was administered at 75 mg/m2 or 100 mg/m2 intravenously every 3 weeks. In certain embodiments, the docetaxel was administered for a minimum of 6 cycles.

In embodiments wherein the patient received prior treatment with a taxane and trastuzumab, and in one embodiment, the trastuzumab may be or was administered at 8 mg/kg intravenously on cycle 1 followed by 6 mg/kg every 3 weeks in subsequent cycles. In another embodiment the trastuzumab may be or was administered at 4 mg/kg intravenously on day 1 of cycle 1 followed by 2 mg/kg weekly starting on day 8 of cycle 1.

In embodiments wherein the patient received prior treatment with a taxane, trastuzumab and pertuzumab, and in one embodiment, the pertuzumab may be or was administered at 840 mg intravenously on day 1 of cycle 1 followed by 420 mg intravenously every 3 weeks in subsequent cycles.

In all embodiments, the anti-HER2-maytansinoid conjugate may be a trastuzumab-maytansinoid conjugate. In certain embodiments, the trastuzumab-maytansinoid conjugate is a trastuzumab-DM1 conjugate. In one embodiment, the trastuzumab-DM1 conjugate is trastuzumab-MCC-DM1. In some embodiments, the trastuzumab-MCC-DM1 is administered every three weeks at 3.6 mg/kg. In other embodiments, the trastuzumab-MCC-DM1 is administered every week at 2.4 mg/kg.

In certain embodiments of the invention, the breast cancer is previously untreated metastatic breast cancer.

BRIEF DESCRIPTION OF THE DRAWINGS

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 5 and 6, respectively): $V_L$ and $V_H$ domains of variant 574/Pertuzumab (SEQ ID Nos. 7 and 8, respectively), and human $V_L$ and $V_H$ consensus frameworks (hum id, light kappa subgroup I, humIII, heavy subgroup III) (SEQ ID Nos. 9 and 10, respectively). Asterisks identify differences between variable domains of Pertuzumab and murine monoclonal antibody 2C4 or between variable domains of Pertuzumab and the human framework. Complementarity Determining Regions (CDRs) are in brackets.

FIGS. 3A and 3B show the amino acid sequences of Pertuzumab light chain (FIG. 3A: SEQ ID NO. 11) and heavy chain (FIG. 3B: SEQ ID No. 12). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIGS. 4A and 4B show the amino acid sequences of Trastuzumab light chain (FIG. 4A: SEQ ID NO. 13) and heavy chain (FIG. 4B: SEQ ID NO. 14), respectively. Boundaries of the variable light and variable heavy domains are indicated by arrows.

FIGS. 5A and 5B depict a variant Pertuzumab light chain sequence (FIG. 5A: SEQ ID NO. 15) and a variant Pertuzumab heavy chain sequence (FIG. 5B: SEQ ID NO. 16), respectively.

DETAILED DESCRIPTION OF EXEMPLARY EMBODIMENTS

Figure 1:
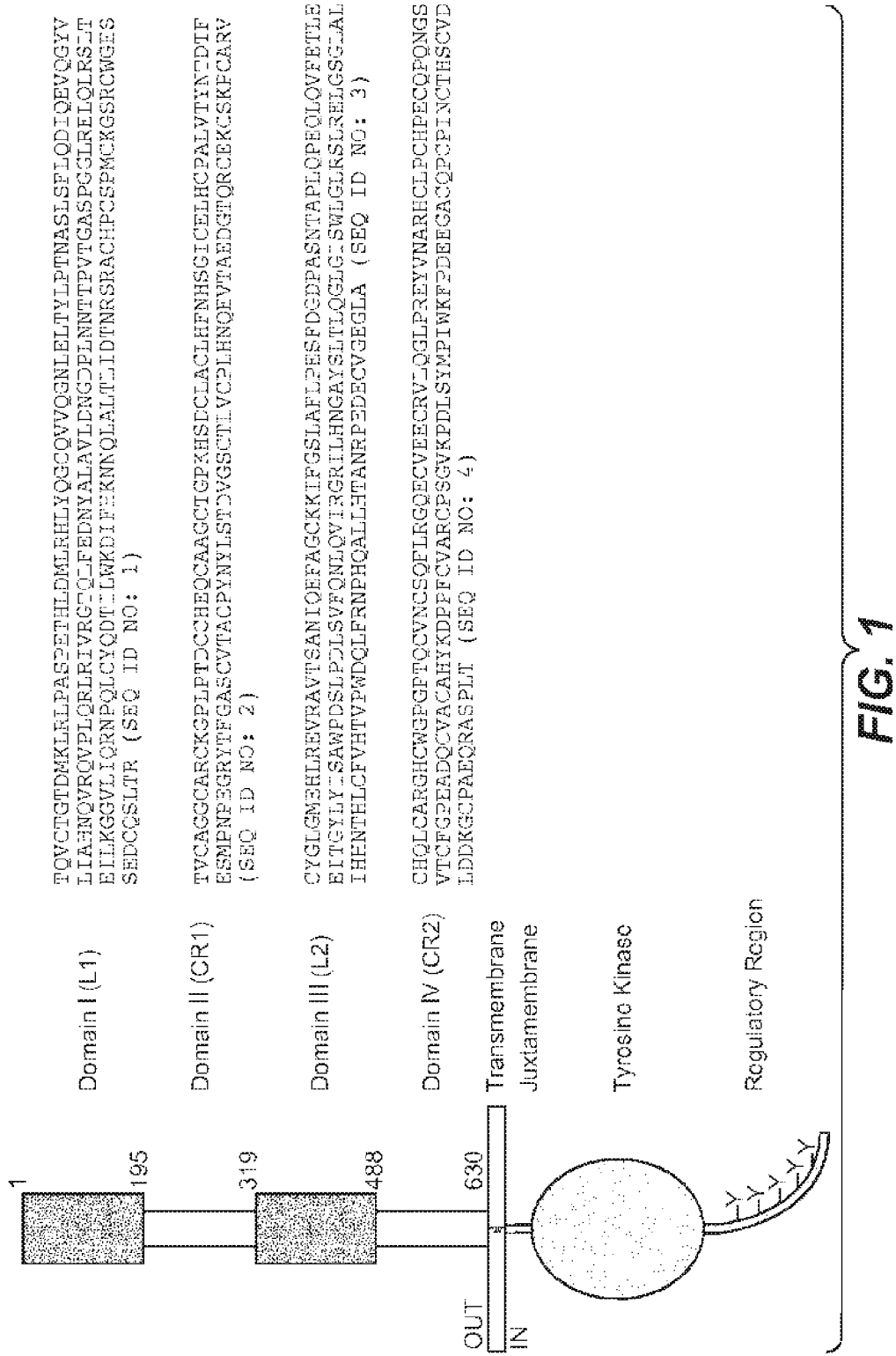
FIG. 1 pros ides a schematic of the HER2 protein structure, and amino acid sequences for Domains I-IV (SEQ ID Nos. 1-4, respectively) of the extracellular domain thereof.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described.

All references cited throughout the disclosure are expressly incorporated by reference herein in their entirety. In the event that one or more of the incorporated literature, patents, and similar materials differs from or contradicts this application, including but not limited to defined terms, term usage, described techniques, or the like, this application controls.

Definitions

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to both therapeutic treatment and prophylactic or preventative measures, wherein the object is to prevent or slow down (lessen) an undesired physiological change or disorder, such as the growth, development or spread of a hyperproliferative condition, such as cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma penile carcinoma, as well as head and neck cancer.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor is known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

The term "first line" metastatic breast cancer or "previously untreated" metastatic breast cancer refers to metastatic breast cancer that has not received treatment in the metastatic selling.

As used herein, the term "locally advanced" breast cancer refers to progressive or recurrent locally advanced breast cancer.

The term "prior treatment," with reference to a taxane, refers to treatment that has occurred prior to the first line metastatic or locally advanced setting. For example, "prior treatment" may refer to treatment in the neoadjuvant, adjuvant or other setting prior to the first line metastatic or locally advanced setting.

An "advanced" cancer is one which has spread outside the site or organ of origin, either by local invasion or metastasis. Accordingly, the term "advanced" cancer includes both locally advanced and metastatic disease.

A "refractory" cancer is one which progresses even though an anti-tumor agent, such as a chemotherapy, is being administered to the cancer patient. An example of a refractory cancer is one which is platinum refractory.

A "recurrent" cancer is one which has regrown, either at the initial site or at a distant site, after a response to initial therapy, such as surgery.

A "locally recurrent" cancer is cancer that returns after treatment in the same place as a previously treated cancer.

An "operable" or "resectable" cancer is cancer which is confined to the primary organ and suitable for surgery (resection).

A "non-resectable" or "unresectable" cancer is not able to be removed (resected) by surgery.

A "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2 or 3 and/or an in situ hybridization (ISH) amplification ratio ≥2,0.

Herein, a "patient" or "subject" is a human patient. The patient may be a "cancer patient." i.e. one who is suffering or at risk for suffering from one or more symptoms of cancer, in particular gastric or breast cancer.

A "patient population" refers to a group of cancer patients. Such populations can be used to demonstrate statistically significant efficacy and/or safety of a drug, such as Pertuzumab.

A "relapsed" patient is one who has signs or symptoms of cancer alter remission. Optionally, the patient has relapsed after adjuvant or neoadjuvant therapy.

A cancer or biological sample which displays HER expression, amplification, or activation is one which, in a diagnostic test, expresses (including overexpresses) a HER receptor, has amplified HER gene, and or otherwise demonstrates activation or phosphorylation of a HER receptor.

"Neoadjuvant therapy" or "preoperative therapy" herein refers to therapy given prior to surgery. The goal of neoadjuvant therapy is to provide immediate systemic treatment potentially eradicating micrometastases that would otherwise proliferate if the standard sequence of surgery followed by systemic therapy were followed. Neoadjuvant therapy may also help to reduce tumor size thereby allowing complete resection of initially unresectable tumors or preserving portions of the organ and its functions. Furthermore, neoadjuvant therapy permits an in vivo assessment of drug efficacy, which may guide the choice of subsequent treatments.

Adjuvant therapy herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

"Progression-Free Survival" (PFS) is the time from the first day of treatment to documented disease progression (including isolated CNS progression) or death from any cause on study, whichever occurs first.

"Disease free survival (DFS)" refers to the patient remaining alive, without return of the cancer, for a defined period of time such as about 1 year, about 2 years, about 3 years, about 4 years, about 5 years, about 10 years, etc. From initiation of treatment or from initial diagnosis. In one aspect of the invention, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g. breast cancer recurrence or second primary cancer).

"Overall survival" refers to the patient remaining alive for a defined period of time, such as about 1 year, about 2 years, about 3 years, about 4 years, about 5 years, about 10 years, etc., from initiation of treatment or from initial diagnosis. In the studies underlying the invention the event used for survival analysis was death from any cause.

By "extending survival" is meant increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

"Hazard ratio" in survival analysis is a summary of the difference between two survival curves, representing the reduction in the risk of death on treatment compared to control, over a period of follow-up. Hazard ratio is a statistical definition for rates of events. For the purpose of the invention, hazard ratio is defined as representing the probability of an event in the experimental arm divided by the probability of an event in the control arm at any specific point in time.

By "monotherapy" is meant a therapeutic regimen that includes only a single therapeutic agent for the treatment of the cancer or tumor during the course of the treatment period.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

"Definitive surgery" is used as that term is used within the medical community. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor. Definitive surgery includes procedures that occurs in one or more stages, and includes, for example, multi-stage surgical procedures where one or more surgical or other procedures are performed prior to resection or the tumor. Definitive surgery includes procedures to remove or resect the tumor including involved organs, parts of organs and tissues, as well as surrounding organs, such as lymph nodes, parts of organs, or tissues.

As defined herein, the terms "trastuzumab", "HERCEPTIN®" and "huMAb4D5-8" are used interchangeably. Such antibody preferably comprises the light and heavy chain amino acid sequences shown in FIG. 4A (SEQ ID NO: 13) and FIG. 4B (SEQ ID NO. 14), respectively.

The "epitope 4D5" or "4D5" epitope or "4D5" is the region in the extracellular domain of HER2 to which the antibody: 4D5 (ATCC CRL 10463) and trastuzumab bind. This epitope is close to the transmembrane domain of HER2, and within Domain IV of HER2. To screen for antibodies which bind to the 4D5 epitope, a routine cross-blocking assay such as that described in Antibodies. A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 520 to about residue 625, inclusive, of HER2).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and Pertuzumab bind to the extracellular domain of HER2 at the junction of domains I, II and III (Franklin et al. *Cancer Cell* 5:317-328 (2004)).

For the purposes herein, "pertuzumab", "PERJETA®" and "rhuMAb 2C4", are used interchangeably. Such antibody preferably comprises the light and heavy chain amino acid sequences in SEQ ID NOs: 7 and 8, respectively. Where Pertuzumab is an intact antibody, it preferably comprises an IgG1 antibody: in one embodiment comprising the light chain amino acid sequence in SEQ ID NO: 11 or 15, and heavy chain amino acid sequence in SEQ ID NO: 12 or 16. The antibody is optionally produced by recombinant Chinese Hamster Ovary (CHO) cells.

As defined herein, the terms "T-DM1," "trastuzumab-MCC-DM1," "ado-trastuzumab emtansine," "trastuzumab emtansine," and "KADCYLA®" are used interchangeably, and refer to trastuzumab linked through the linker moiety MCC to the mavtansinoid drug moiety DM1, including all mixtures of variously loaded and attached antibody-drug conjugates where 1, 2, 3, 4, 5, 6, 7, and 8 drug moieties are covalently attached to the antibody trastuzumab (U.S. Pat. No. 7,097,840: US 2005/0276812: US 2005/0166993).

Herein, an "anti-tumor agent" refers to a drug used to treat cancer. Non-limiting examples of anti-tumor agents herein include chemotherapy agents. HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125. HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

A "chemotherapy" is use of a chemotherapeutic agent useful in the treatment of cancer.

A "chemotherapeutic aunt" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Examples of chemotherapeutic agents include: erlotinib (TARCEVA®, Genentech/OSI Pharm.), docetaxel (TAXOTERE®, Sanofi-Aventis). 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton. N. J.), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenlbut-1-enyl)phenoxy]-N,N-dimethyl-ethanamine. NOLVADEX®, ISTUBAL®, VALODEX®), and doxorubicin (ADRIAMYCIN®), Akti-½, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SUII248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semalore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafamib (SARASAR™, SCH 66336, Schering Plough), serafenib (NEXAVAR®, BAY43-9006, Bayer Labs), gefitinib (IRESSA®, AstraZeneca), irinotecan (CAMPTOSAR®, CPT-22 Pfizer), tipifarnib (XARNESTRA™, Johnson & Johnson), ABRAXANE™ (Cremophor-free), albumin-engineered nanoparticle formulations of paclitaxel (American Pharmaceutical Partners, Schaumberg, 11), vandetanib (rINN, ZD6474, ZACTIMAN®, AstraZeneca), chloranmbucil, AG1478, AG1571 (SU 5271: Swaim), temsirolimus (TORISEL®, Wyeth), pazopanib (GlaxoSmithKline), canfosfamide (TELCYTA®, Telik), thiotepa and cyclosphosphamide (CYTOXA®, NEOSAR®); alkyl sulfonates such as busulfan, improsul fan and piposulfan, aziridines such as bermodopa, carboquone, nneturedopa, and uredopa: ethylenimines and methylamelamines including altretamine, triethylenemelamine, triethylenephosphoramide, triethylenethiophosphoramide and trimethylomelamine: acetogenins (especially bullatacin and bullatacinone): a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic KW-2189 and CB1-TM1): cleutherobin: pancratistatin: a sarcodictyin: spongistatin: nitrogen mustards such as chlorambucil, chlornaphazine, chlorophosphamide, estramustine, ifosfamide, mechlorothamine, mechlorethamine oxide hydrochloride, melphalan, noycmbichin, phenesterinc, prednimustine, trofosfamide, uracil mustard: nitrosoureas such as carmustine, chlorozotocin, fotemustine, lomustine, nimustine, and ranimnustine; antibiotics such as the enedivne antibiotics (e.g., calichcamicin, calichcarnicin gamma II, calichearnicin omegaII (Angrew Chem. Intl. Ed. Engl. (1994) 33:183-186): dynemicin, dynetricin bisphosphonates, such as clodronate: an esperamicin: as well as neocarzinostatin chromophore and related chromoprotein cnedivne antibiotic chromophores), aclacinomvsins, actinomycin, authramycin, azaserine, bleomycins, cactinomycin, carabicin, carminomycin, carzinophilin, chromonnycinis, dactinormycin, daunorubicin, detorubicin, 6-diazo-5-oxo-L-norleucine, morpholine-doxorubicin, cyanomorpholino-doxorubicin, 2-pyrrolino-doxorubicin and deoxydoxorubicin), epirubicin, esorubicin, idarubicin, marcellonnyein, mitomycins such as milomycin C, mycophenolic acid, nogalamycin, oliyomycins, peplomycin, porfiromycin, puromycin, quelamycin, rodorubicin, streptonigrin, streptozocin, tubercidin, ubenimex, zorubicin: anti-metabolites such as methotrexate and 5-fluorouracil (5-FU): Folic acid analogs such as denopterin, methotrexate, pteropterin, trimetrexate: purine analogs such as fludarabine, 6-mercaptopurine, thiamiprine, thioguanine: pyrimidine analogs such as ancitabinc, azacitidine, 6-azauridine, carmofur, cytarabine, dideoxyuridine, doxifluridinc, enocitabine, floxuridine: androgens such as calusterone, dromostanolone propionate, epitiostanol, mepitiostane, testolactone: anti-adrenals such as aminoglutethimide, milotane, trilostane: folic acid replenisher such as frolinic acid: aceglatone: aldophosphamide alvcoside: aminoglevulinic acid: eniluracil: amsacrine: bestrabucil: bisantrene: edatraxate: defofamine: demecolcine: diatiquone: elromithine: elliptinium acetate: an epothilone: etoglucid: gallium nitrate: hydroxyurea: lentinan: lonidainine: maytansinoids such as maytansine and ansamitocins: mitoguazone: mitoxantrone: mopidanmol: nitracrine: pentostatin: phenamet: pirarubicin: losoxantrone: podophyllinic acid: 2-ethylhydrazide: procarbazine, PSK®, polysaccharide complex (JHS Natural Products, Eugene, Oreg.): razoxane: rhizoxin: sizofiran: spirogerrnanium: tenuazonic acid: triaziquone: 2,2',2''-trichlorotriethdamine: trichothecenes (T-2 toxin, verracurin A. roridin A and anguidine): urethan: vindesine: dacarbazine: mannomustine: mitobronitol: mitolactol: pipobroman: gacytosine: arabinoside (Ara-C): cyclophosphamide: thiotepa: 6-thioguanine: mercaptopurine: methotrexate: platinum analogs such as cisplatin and carboplatin: vinblastine: etoposide (VP-16): ifosfamide: mitoxantrone: vincristine: vinorelbine (NAVELBINE®): noravantrone: teniposide: edatrexate: daunomycin: aminopterin: capecitahine (XELODA®, Roche): ibandronate: CPT-11: topoisomerase inhibitor RFS 2000: difluoromethylomithine (DMFO): retinoids such as retinoic acid: and pharmaceutically acceptable salts, acids and derivatives of any of the above.

The term "effective amount" refers to an amount of a drug effective to treat cancer in the patient. The effective amount of the drug may reduce the number of cancer cells: reduce the tumor size: inhibit (i.e., slow to some extent and preferably stop) cancer cell infiltration into peripheral organs: inhibit (i.e., slow to some extent and preferably stop) tumor metastasis: inhibit, to some extent, tumor growth: and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI). The term "effective amount" specifically includes an amount suitable for achieving any of the primary or secondary endpoints of the clinical trial described in Example 1.

A "taxane" is a chemotherapy which inhibits mitosis and interferes with microtubules. Examples or taxanes include paclitaxel (TAXOLIO: Bristol-Myers Squibb Oncology, Princeton, N.J.): cremophor-free, albumin-engineered nanoparticle formulation of paclitaxel or nab-paclitaxel (ABRAXANE™: American Pharmaceutical Partners, Schaumberg, Ill.): and docetaxel (TAXOTERE®: Rhône-Poulenc Rorer, Anton, France).

An "anthacycline" is a type of antibiotic that comes from the fungus *Streptococcus peucetius*, examples include: daunorubicin, doxorubicin, and epirubicin, etc.

"Anthracycline-based chemotherapy" refers to a chemotherapy regimen that consists of or include one or more anthracyclinc. Examples include 5-FU, epirubicin, and cyclophosphamide (FEC): 5-FU, doxorubicin, and cyclophosphamide (FAC): doxoruhicin and cyclophosphamide (AC): epirubicin and cyclophosphamide (EC): etc.

For the purposes herein, "carboplatin-based chemotherapy" refers to a chemotherapy regimen that consists of or includes one or more carboplatins. An example is TCH (docetaxel/TAXOL®, carboplatin, and trastuzumab/HERCEPTIN®).

An "aromatase inhibitor" inhibits the enzyme aromatase, which regulates estrogen production in the adrenal glands. Examples of aromatase inhibitors include: 4(5)-imidazoles, aminoglutethimide, MEGASE® megestrol acetate, AROMASIN® exemestane, formestane, fadrotole, RIVISOR® yorozole, FEMARA® letrotole, and ARIMIDEX® anastrozole. In one embodiment the aromatase inhibitor herein is letrotole or anastrozole.

An "antimetabolite chemotherapy" is use of an agent which is structurally similar to a metabolite, but can not be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecilabine (XELODA™), 6-mercaptopurine, methotrexate, 6-thioguanine, pernetrexed, raltitrexed, arabinosylcytosine ARA-C cytarabine (CYTOSAR-U®), dacarbazine (DTIC-DOME®), atocytosine, deoxycytosine, pyrimidine, fludarabine (FLUDARA10), cladribine, 2-deoxy-D-glucose etc.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

The term "platin" is used herein to refer to platinum based chemotherapy, including without limitation cisplatin, carboplatin, and oxaliplatin.

The term "fluoropyrimidine" is used herein to refer to an antimetabolite chemotherapy, including, without limitation, capecitabine, floxuridine and fluorouracil (5-FU).

A "fixed" or "flat" dose of a therapeutic agent herein refers to a dose that is administered to a human patient without regard for the weight (WT) or body surface area (RSA) of the patient. The fixed or flat dose is therefore not provided as a mg/kg dose or a mg/m$^2$ dose, but rather as an absolute amount of the therapeutic agent.

A "loading" dose or "LD" herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

"Infusion" or "infusing" refers to the introduction of a drug-containing solution into the body through a vein for therapeutic purposes. Generally, this is achieved via an intravenous (IV) bag.

An "intravenous bag" or "IV bag" is a bag that can hold a solution which can be administered via the vein of a patient. In one embodiment, the solution is a saline solution (e.g. about 0.9% or about 0.45% NaCl). Optionally, the IV bag is formed from polyolefin or polyvinal chloride.

By "co-administering" is meant intravenously administering two (or more) drugs during the same administration, rather than sequential infusions of the two or more drugs. Generally, this will involve combining the two (or more) drugs into the same IV bag prior to co-administration thereof.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

"Cardiac toxicity" refers to any toxic side effect that affects the heart and that results from administration of a drug or drug combination. Cardiac toxicity can be evaluated based on any one or more of: incidence of symptomatic left ventricular systolic dysfunction (LVSD) or congestive heart failure (CHF), or decrease in left ventricular ejection fraction (LVEF).

The phrase "without increasing cardiac toxicity" for a drug combination including pertuzumab refers to an incidence of cardiac toxicity that is equal or less than that observed in patients treated with drugs other than pertuzumab in the drug combination (e.g. equal or less than that resulting from administration of trastuzumab and the chemotherapy. e.g. docetaxel).

A "vial" is a container suitable for holding a liquid or lyophilized preparation. In one embodiment, the vial is a single-use vial, e.g. a 20-cc, single-use vial with a stopper.

The term "package insert" is used to refer to instructions customarily included in commercial packages of therapeutic products, that contain information about the indications, usage, dosage, administration, contraindications and/or warnings concerning the use of such therapeutic products.

An "adverse event" is any unfavorable and unintended sign, symptom, or disease temporally associated with the use of an investigational (medicinal) product or other protocol-imposed intervention, regardless of attribution; and includes: AEs not previously observed in the patient that emerge during the protocol-specified AE reporting period including signs or symptoms associated with breast cancer that were not present before the AE reporting period: complications that occur as a result of protocol-mandated interventions (e.g., invasive procedures such as biopsies); if applicable, AEs that occur before assignment of study treatment associated with medication washout, no treatment run-in, or other protocol-mandated intervention: Preexisting medical conditions (other than the condition being studied) judged by the investigator to have worsened in severity or frequency or changed in character during the protocol-specified AE reporting period An adverse event is classified as a "Serious Adverse Events" (SAE) if it meets the following criteria: results in death (i.e., the AE actually causes or leads to death): life threatening (i.e., the AE in the view of the investigator places the patient at immediate risk of death, but not including an AE that, had it occurred in a more severe form, might have caused death): requires or prolongs inpatient hospitalisation: results in persistent or significant disability/incapacity (i.e., the AE results in substantial disruption of the patient's ability to conduct normal life functions): results in a congenital anomaly/birth defect in a neonate/infant born to a mother exposed to the investigational product: or is considered a significant medical even by the investigator based on medical judgment (e.g., may jeopardize the patient or may require medical/surgical intervention to prevent one of the outcomes listed above). All AEs that do not meet any of the criteria for serious are regarded as non-serious AEs. The terms "severe" and "serious" are not synonymous. Severity (or intensity) refers to the grade of a specific AE. e.g., mild (Grade 1), moderate (Grade 2), or severe (Grade 3) myocardial infarction (see Section 5.2.2). "Serious" is a regulatory definition (see previous definition) and is based on patient or event outcome or action criteria usually associated with events that pose a threat to a patients life or functioning. Seriousness (not severity) serves as the guide for defining regulatory reporting obligations from the Sponsor to applicable regulatory authorities. Severity and seriousness should be independently assessed when recording AEs and SAEs on the eCRT.

Detailed Description

The present invention is based, in part, on the observation that trastuzumab-MCC-DM1 was unexpectedly effective in treating patients with first line metastatic HER2-positive breast cancer, where the patients had received prior treatment with a taxane, compared with patients who had not received prior taxane. The present invention provides methods of using anti HER2-maytansinoid conjugates, such as trastuzumab-MCC-DM1. For the treatment of HER2-positive progressive or recurrent locally advanced or previously untreated metastatic breast cancer (first line metastatic breast cancer), where the patient has been previously treated with a taxane. Although treatment options exist for HER2-positive cancer patients in the adjuvant neo-adjuvant and metastatic settings, further options are needed, including in the "first line" metastatic setting, i.e., for patients with previously untreated metastatic breast cancer, or patients with locally advanced breast cancer. Overall, T-DM1 demonstrated non-inferior progression free survival (PFS) compared with standard-of-care HERCEPTIN taxane (HT), but it was not superior to HT. However, data suggest an effect favoring T-DM1 over HT for patients who had previously received taxane therapy, indicating that such patients should be selected for treatment with anti-HER2-maytansinoid conjugates, such as trastuzumab-MCC-DM1, for locally advanced and first line metastatic Her2-positive breast cancer.

Trastuzumab-MCC-DM1 (T-DM1)

The present invention includes therapeutic treatments with trastuzumab-MCC-DM1 (T-DM1), an antibody-drug conjugate (CAS Reg. No. 139504-50-0), which has the structure:

bodies include huMAb4D5-1 huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

Trastuzumab-MCC-DM1 may be prepared according to Example 1 of U.S. Application Publication No. 20110105155, for example.

Formulations of Anti-HER2-Maytansinoid Conjugates

Anti-HER2-maytansinoid conjugates, such as trastuzumab-MCC-DM1, may be formulated in accordance with standard pharmaceutical practice for use in a therapeutic combination. The pharmaceutical compositions comprise trastuzumab-MCC-DM1 in association with one or more pharmaceutically acceptable carrier, glidant, diluent, or excipient.

Suitable carriers, diluents and excipients are well known to those skilled in the art and include materials such as carbohydrates, waxes, water soluble rind/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to

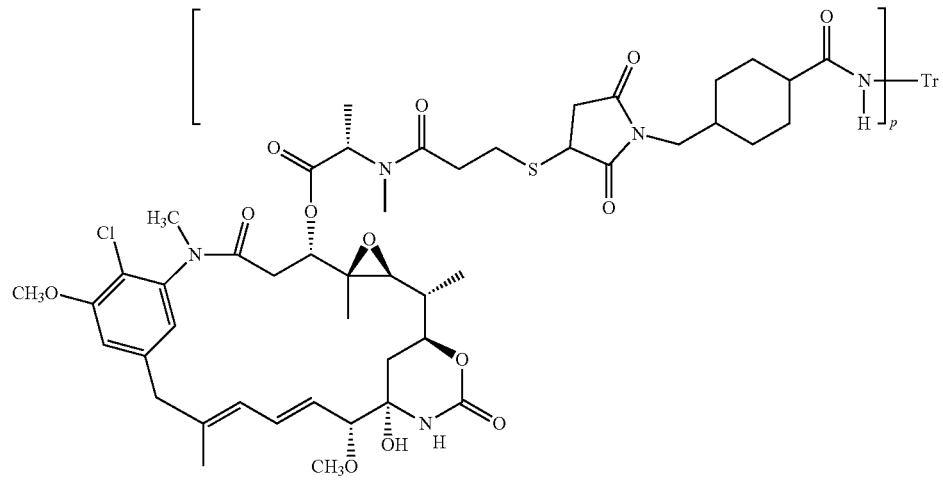

where Tr is trastuzumab linked through linker moiety MCC to the maytansinoid drug moiety DM1 (U.S. Pat. No. 5,208,020: U.S. Pat. No. 6,441,163). The drug to antibody ratio or drug loading is represented by p in the above structure of trastuzumab-MCC-DM1, and ranges in integer clues from 1 to about 8. Trastuzumab-MCC-DM1 includes all mixtures of variously loaded and attached antibody-drug conjugates where 1, 2, 3, 4, 5, 6, 7, and 8 drug moieties are covalenth attached to the antibody trastuzumab (U.S. Pat. No. 7,097,840: US 2005/0276812: US 2005/0166993). Average drug load is about 3.5.

Trastuzumab can be produced by a mammalian cell (Chinese Hamster Ovary, CHO) suspension culture. The HER2 (or c-erbB2) proto-oncogene encodes a transmembrane receptor protein of 185 kDa, which is structurally related to the epidermal growth factor receptor. Trastuzumab is an antibody that has antigen binding residues of, or derived from, the murine 4D5 antibody (ATCC CR1: 10463, deposited with American Type Culture Collection, 12301 Parklawn Drive, Rockville, Md. 20852 under the Budapest Treaty on May 24, 1990). Exemplary humanized 4D5 antibe administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration with pharmaceutically acceptable diluents, carriers, excipients or stabilizers (Remington's Pharmaceutical Sciences (1995) 18th edition. Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids: antioxidants including ascorbic acid and methionine: preservatives (such as octadecyldimethylbenzyl ammonium chloride: hexamethonium chloride: benzalkonium chloride, benzethonium chloride: phenol, butyl, ethanol, or benzylalcohol: alkyl parabens such as methyl or propyl paraben: catechol: resorcinol: cyclohexanol, 3-pentanol: and m-cresol): low molecular weight (less than about 10 residues) polypeptides: proteins, such as serum albumin, gelatin, or immunoglobulins: hydrophilic polymers such as polyvinylpyrrolidone: amino acids such as glycine, glutamine, asparagine, histidine, arginine, or lysine: monosaccharides, disaccharides and other carbohydrates including glucose, mannose, or dextrins: chelating agents such as EDTA: sugars such as sucrose, mannitol, trehalose or sorbitol: salt-forming counter-ions such as sodium: metal complexes (e.g., Zn-protein complexes): and/or non-ionic surfactants such as TWEEN™, including Tween™ 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co. Easton, Pa. Other examples of drug formulations can be found in Liberman, H. A. and Lachman, Eds., Pharmaceutical Dosage Forms, Marcel Decker. Vol 3, $2^{nd}$ Ed., New York, N.Y.

The pharmaceutical formulations include those suitable for the administration routes detailed herein. The formulations may conveniently be presented in unit dosage form and may be prepared by any of the methods well known in the art of pharmacy. Techniques and formulations generally are Found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient: and aqueous and non-aqueous sterile suspensions which may include suspending agents and thickening agents.

The formulations may be packaged in unit-dose or multi-dose containers, for example scaled ampoules and vials, and may be stored in a freeze-dried (lyophilized) condition requiring, only the addition of the sterile liquid carrier for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

As a general proposition, the initial pharmaceutically effective amount of trastuzumab-MCC-DM1 administered per dose will be in the range of about 0.3 to 15 mg/kg/day of patient body weight.

A commercial T-DM1 Formulation (KADCYLA®, ado-trastuzumab emtansine) is a sterile, white to off-white preservative free lyophilized powder in single-use vials. Each vial contains 100 mg or 160 mg ado-trastuzumab emtansine. Following reconstitution, each single-use vial contains ado-trastuzumab emtansine (20 mg/mL), polysorbate 20 [0.02% (w/v)], sodium succinate (10 mM), and sucrose [6% (w/v)] with a pH of 5.0 and density of 1,026 g/mL. The resulting solution containing 20 mg/mL adotrastuzumab emtansine is administered by intravenous infusion following dilution.

Formulation of Pertuzumab

A commercial formulation of pertuzumab (PERJETA®) contains pertuzumab 420 mg/14 mL (30 mg/mL) in the form of a preservative-free solution for IV infusion.

Administration of Pharmaceutical Compostions

Pharmaceutical compositions described herein may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. For local immunosuppressive treatment the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

Articles of Manufacture

Articles of manufacture, or "kits", containing anti-HER2-maytansinoid conjugates, such as trastuzumab-MCC-DM1, are useful for the treatment methods herein are provided. In one embodiment the kit comprises a container comprising trastuzumab-MCC-DM1. The kit may further comprise a label or package insert, on or associated with the container. The term "package insert" is used to refer to instructions customarily included in commercial packages of therapeutic products, that contain information about the indications, usage, dosage, administration contraindications and/or warnings concerning the use of such therapeutic products. Suitable containers include, for example, bottles, vials, syringes, blister pack, etc. The container may be formed from a variety of materials such as glass or plastic. The container may hold an anti-HER2-maytansinoid conjugate, such as trastuzumab-MCC-DM1, or a formulation thereof which is effective for use in a treatment method herein, and may have a sterile access port (for example, the container may be an intravenous solution hag or a vial having a stopper pierceable by a hypodermic injection needle). The label or package insert indicates that the composition is used in a treatment method as described and claimed herein. The article of manufacture may also contain a further container comprising a pharmaceutically acceptable buffer, such as bacteriostatic water for injection (WEI), phosphate-buffered saline. Ringer's solution and dextrose solution. It may further include other materials desirable from a commercial and user standpoint, including other buffers, diluents, filters, needles, and syringes.

The kit may further comprise directions for the administration of trastuzumab-MCC-DM1. For example, if the kit comprises a first composition comprising trastuzumab-MCC-DM1 and a second pharmaceutical formulation, the kit may further comprise directions for the simultaneous, sequential or separate administration of the First and second pharmaceutical compositions to a patient in need thereof.

EXAMPLES

In order to illustrate the invention, examples are included as provided in the Figures, the foregoing Brief Description of the Drawings, and the examples below. However, it is to be understood that these examples do not limit the invention and are only meant to suggest a method of practicing the invention.

Example 1

Phase III Clinical Study

Figure 6:
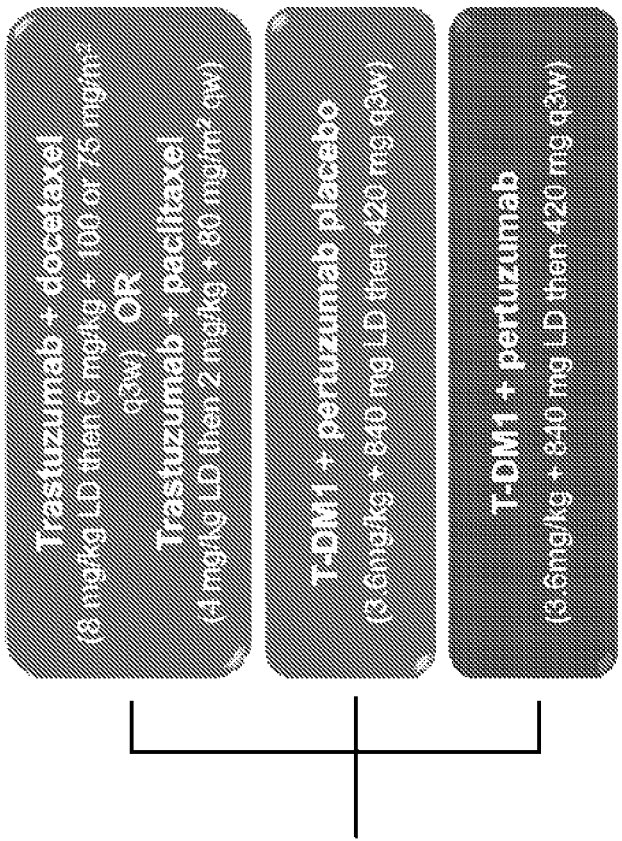
FIG. 6 depicts the schema of the MARIANNE clinical trial design described in Example 1. [a]Locally progressive or recurrent and not amenable to resection with curative intent: [b]Pertuzumab placebo. LD, loading dose.

This study (clinicaltrials.gov identifier #NCT01120184: study number BO22589) is a randomized, 3-arm, multi-centre, phase III study that evaluated the efficacy and safety of trastuzumab emtansine (T-DM 1) with pertuzumab, or trastuzumab emtansine (T-DM 1) alone (i.e., with pertuzumab-placebo), versus the combination of trastuzumab (Herceptin) plus taxane (docetaxel or paclitaxel) in patients with HER2-positive progressive or recurrent locally advanced or previously untreated metastatic breast cancer (See FIG. 6).

Stratification factors: World region. Prior neo-adjuvant therapy (if Yes: prior trastuzumab/lapatinib). Visceral disease.

Primary end point: Progression-Free Survival (PFS) by independent review facility (IRF), non-inferiority and superiority assessed.

Key secondary end points: Overall Survival (OS). PFS by investigator, Objective Response Rte (ORR). Safety. Patient-reported outcomes.

The inclusion and exclusion criteria for this study are as follows:

Criteria

The inclusion criteria are as follows: 1) Adult patients >/18 years of age: 2) HER2-positive breast cancer: 3) Histologically or cytologically confirmed adenocarcinoma of the breast with locally recurrent or metastatic disease, and be a candidate for chemotherapy. Patients with locally advanced disease must hay e recurrent or progressive disease, which must not be amenable to resection with curative intent: 4) Patients must have measurable and/or non-measurable disease which must be valuable per RECIST 1.1: 5) ECOG Performance Status 0 or 1: 6) Adequate organ function as determined by laboratory results.

The exclusion criteria are as follows: 1) History of prior (or any) chemotherapy for metastatic breast cancer or recurrent locally advanced disease: 2) An interval or <6 months from the last dose of vinca-alkaloid or taxane cytotoxic chemotherapy until the time of metastatic diagnosis: 3) Hormone therapy <7 days prior to randomization: 4) Trastuzumab therapy and/or lapatinib (neo- or adjuvant setting) <21 days prior to randomization: 5) Prior trastuzumab emtansine or pertuzumab therapy.

Outcome Measures were as Follows:

Primary outcomes were assessed using the following measures: 1) Progression Free Survival (PFS) based on tumor assessments performed by an Independent Review Facility (IRF), and 2) Incidence of adverse events (AEs).

Secondary outcomes were assessed using the following measures: 1) Overall Survival (OS) truncated at 2 scars. 2) 1-rear survival rate: 3) Overall Survival (OS) rate: 4) Overall or objective response rate: 5) Duration of response: 6) Time-to-Treatment Failure as assessed by Independent Review Facility (IRF): and 7) Clinical benefit rate.

Figure 7:
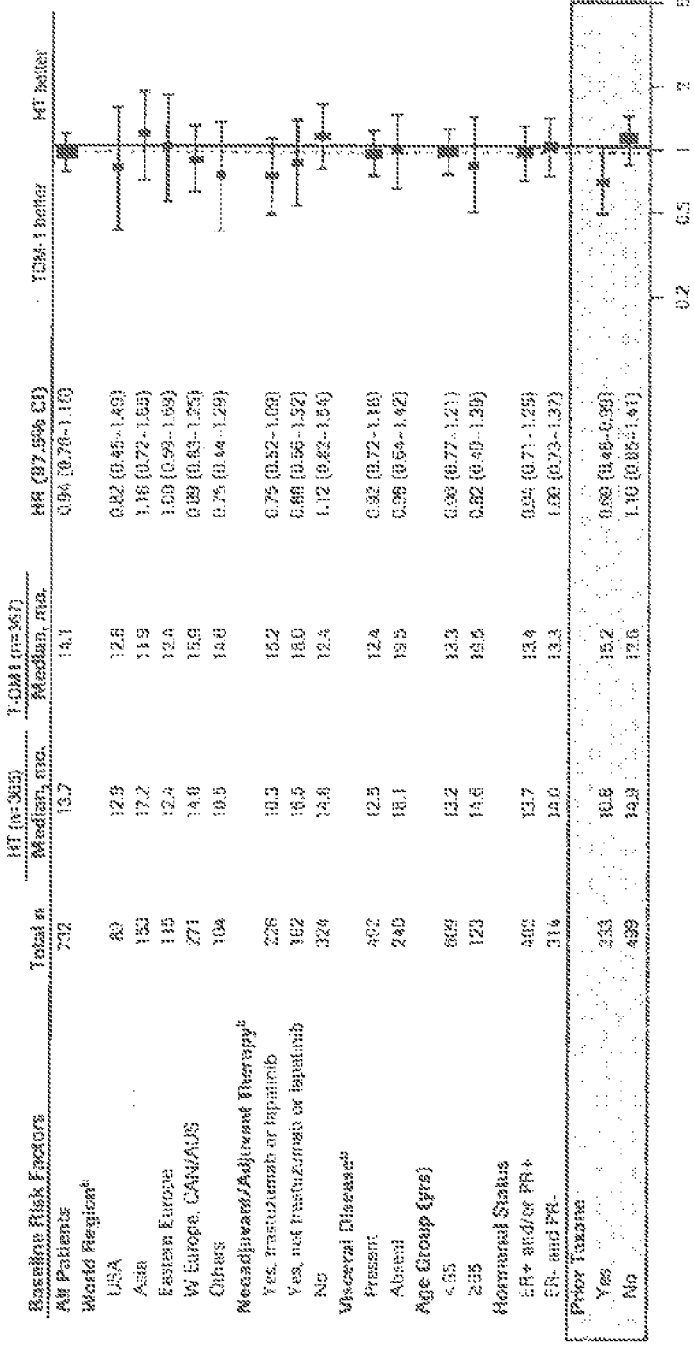
FIG. 7 shows results from the MARIANNE clinical trial described in Example 1. Overall, T-DM1 (KADCYLA®) demonstrated non-inferior progression free survival (PFS) compared with standard-of-care trastuzumab (HERCEPTIN®); taxane (HT), but it was not superior to HT. However, data (shaded box) suggest an effect favoring KADCYLA® over HT for patients who had previously received taxane therapy, indicating that such patients should be selected for treatment with KADCYLA® for locally advanced and first line metastatic Her2-positive breast cancer.

As shown in FIG. 7, data suggests an effect favoring T-DM1 (Kadcyla®) for patients with first line metastatic HER2-positive breast cancer who had previously received taxane therapy.

We claim:

1. A method of treating HER2-positive locally advanced or metastatic breast cancer, the method comprising administering to a patient having the HER2-positive locally advanced or metastatic breast cancer a therapeutically effective amount of an anti-HER2-maytansinoid conjugate,
    wherein the patient received prior treatment of a locally non-advanced and non-metastatic HER2-positive breast cancer with a taxane prior to progression to positive locally advanced or metastatic disease and the last prior dose of the taxane treatment was at least ≥6 months before administration of the anti-HER2-maytansinoid conjugate, and
    wherein after the patient's cancer progressed to HER2-positive locally advanced or metastatic disease but prior to treatment with the anti-HER2-maytansinoid conjugate, the patient has not been treated with any chemotherapy.

2. The method of claim 1, wherein the patient received prior treatment with a taxane and at least one HER2-directed therapy.

3. The method of claim 2, wherein the patient received prior treatment with a taxane and trastuzumab.

4. The method of claim 3, wherein the patient received prior treatment with a taxane, trastuzumab, and pertuzumab.

5. The method of any of claims 1 and 2-4, wherein the prior treatment was administered in the adjuvant setting.

6. The method of any of claims 1 and 2-4, wherein the prior treatment was administered in the neoadjuvant setting.

7. The method of any of claims 1 and 2-4, wherein the taxane is paclitaxel.

8. The method of claim 7, wherein the paclitaxel was administered at 80 mg/m2 intravenously weekly.

9. The method of claim 8, wherein the paclitaxel was administered for a minimum of 18 weeks.

10. The method of any of claims 1 and 2-4, wherein the taxane is docetaxel.

11. The method of claim 10, wherein the docetaxel was administered at 75 mg/m2 or 100 mg/m2 intravenously every 3 weeks.

12. The method of claim 11, wherein the docetaxel was administered for a minimum of 6 cycles.

13. The method of claim 3 or 4, wherein the trastuzumab was administered at 8 mg/kg intravenously on cycle 1 followed by 6 mg/kg every 3 weeks in subsequent cycles.

14. The method of claim 3 or 4, wherein the trastuzumab was administered at 4 mg/kg intravenously on day 1 of cycle 1 followed by 2 mg/kg weekly starting on day 8 of cycle 1.

15. The method of claim 4, wherein the pertuzumab was administered at 840 mg intravenously on day 1 of cycle 1 followed by 420 mg intravenously even 3 weeks in subsequent cycles.

16. The method of any of claims 1 and 2-4, wherein the anti-HER2-maytansinoid conjugate is a trastuzumab-maytansinoid conjugate.

17. The method of claim 16, wherein the trastuzumab-maytansinoid conjugate is a trastuzumab-DM1 conjugate.

18. The method of claim 17, wherein the trastuzumab-DM1 conjugate is trastuzumab-MCC-DM1.

19. The method of claim 18, wherein the trastuzumab-MCC-DM1 is administered every three weeks at 3.6 mg/kg.

20. The method of claim 18, wherein the trastuzumab-MCC-DM1 is administered every week at 2.4 mg/kg.

* * * * *

SEQUENCE LISTING

```
<160> NUMBER OF SEQ ID NOS: 16

<210> SEQ ID NO 1
<211> LENGTH: 195
<212> TYPE: PRT
<213> ORGANISM: Homo sapiens

<400> SEQUENCE: 1

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg
        195

<210> SEQ ID NO 2
<211> LENGTH: 124
<212> TYPE: PRT
<213> ORGANISM: Homo sapiens

<400> SEQUENCE: 2

Thr Val Cys Ala Gly Gly Cys Ala Arg Cys Lys Gly Pro Leu Pro Thr
1               5                   10                  15

Asp Cys Cys His Glu Gln Cys Ala Ala Gly Cys Thr Gly Pro Lys His
            20                  25                  30
```

```
Ser Asp Cys Leu Ala Cys Leu His Phe Asn His Ser Gly Ile Cys Glu
        35                  40                  45

Leu His Cys Pro Ala Leu Val Thr Tyr Asn Thr Asp Thr Phe Glu Ser
 50                  55                  60

Met Pro Asn Pro Glu Gly Arg Tyr Thr Phe Gly Ala Ser Cys Val Thr
 65                  70                  75                  80

Ala Cys Pro Tyr Asn Tyr Leu Ser Thr Asp Val Gly Ser Cys Thr Leu
                 85                  90                  95

Val Cys Pro Leu His Asn Gln Glu Val Thr Ala Glu Asp Gly Thr Gln
                100                 105                 110

Arg Cys Glu Lys Cys Ser Lys Pro Cys Ala Arg Val
            115                 120
```

<210> SEQ ID NO 3
<211> LENGTH: 169
<212> TYPE: PRT
<213> ORGANISM: Homo sapiens

<400> SEQUENCE: 3

```
Cys Tyr Gly Leu Gly Met Glu His Leu Arg Glu Val Arg Ala Val Thr
 1               5                  10                  15

Ser Ala Asn Ile Gln Glu Phe Ala Gly Cys Lys Lys Ile Phe Gly Ser
                20                  25                  30

Leu Ala Phe Leu Pro Glu Ser Phe Asp Gly Asp Pro Ala Ser Asn Thr
            35                  40                  45

Ala Pro Leu Gln Pro Glu Gln Leu Gln Val Phe Glu Thr Leu Glu Glu
 50                  55                  60

Ile Thr Gly Tyr Leu Tyr Ile Ser Ala Trp Pro Asp Ser Leu Pro Asp
 65                  70                  75                  80

Leu Ser Val Phe Gln Asn Leu Gln Val Ile Arg Gly Arg Ile Leu His
                 85                  90                  95

Asn Gly Ala Tyr Ser Leu Thr Leu Gln Gly Leu Gly Ile Ser Trp Leu
                100                 105                 110

Gly Leu Arg Ser Leu Arg Glu Leu Gly Ser Gly Leu Ala Leu Ile His
            115                 120                 125

His Asn Thr His Leu Cys Phe Val His Thr Val Pro Trp Asp Gln Leu
130                 135                 140

Phe Arg Asn Pro His Gln Ala Leu Leu His Thr Ala Asn Arg Pro Glu
145                 150                 155                 160

Asp Glu Cys Val Gly Glu Gly Leu Ala
                165
```

<210> SEQ ID NO 4
<211> LENGTH: 142
<212> TYPE: PRT
<213> ORGANISM: Homo sapiens

<400> SEQUENCE: 4

```
Cys His Gln Leu Cys Ala Arg Gly His Cys Trp Gly Pro Gly Pro Thr
 1               5                  10                  15

Gln Cys Val Asn Cys Ser Gln Phe Leu Arg Gly Gln Glu Cys Val Glu
                20                  25                  30

Glu Cys Arg Val Leu Gln Gly Leu Pro Arg Glu Tyr Val Asn Ala Arg
            35                  40                  45

His Cys Leu Pro Cys His Pro Glu Cys Gln Pro Gln Asn Gly Ser Val
 50                  55                  60
```

```
Thr Cys Phe Gly Pro Glu Ala Asp Gln Cys Val Ala Cys Ala His Tyr
 65                  70                  75                  80

Lys Asp Pro Pro Phe Cys Val Ala Arg Cys Pro Ser Gly Val Lys Pro
                 85                  90                  95

Asp Leu Ser Tyr Met Pro Ile Trp Lys Phe Pro Asp Glu Glu Gly Ala
            100                 105                 110

Cys Gln Pro Cys Pro Ile Asn Cys Thr His Ser Cys Val Asp Leu Asp
        115                 120                 125

Asp Lys Gly Cys Pro Ala Glu Gln Arg Ala Ser Pro Leu Thr
    130                 135                 140
```

<210> SEQ ID NO 5
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Asp Thr Val Met Thr Gln Ser His Lys Ile Met Ser Thr Ser Val Gly
 1               5                  10                  15

Asp Arg Val Ser Ile Thr Cys Lys Ala Ser Gln Asp Val Ser Ile Gly
                20                  25                  30

Val Ala Trp Tyr Gln Gln Arg Pro Gly Gln Ser Pro Lys Leu Leu Ile
            35                  40                  45

Tyr Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln Tyr Tyr Ile Tyr Pro Tyr
                 85                  90                  95

Thr Phe Gly Gly Gly Thr Lys Leu Glu Ile Lys
            100                 105
```

<210> SEQ ID NO 6
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Glu Val Gln Leu Gln Gln Ser Gly Pro Glu Leu Val Lys Pro Gly Thr
 1               5                  10                  15

Ser Val Lys Ile Ser Cys Lys Ala Ser Gly Phe Thr Phe Thr Asp Tyr
                20                  25                  30

Thr Met Asp Trp Val Lys Gln Ser His Gly Lys Ser Leu Glu Trp Ile
            35                  40                  45

Gly Asp Val Asn Pro Asn Ser Gly Ser Ile Tyr Asn Gln Arg Phe
 50                  55                  60

Lys Gly Lys Ala Ser Leu Thr Val Asp Arg Ser Ser Arg Ile Val Tyr
 65                  70                  75                  80

Met Glu Leu Arg Ser Leu Thr Phe Glu Asp Thr Ala Val Tyr Tyr Cys
                 85                  90                  95

Ala Arg Asn Leu Gly Pro Ser Phe Tyr Phe Asp Tyr Trp Gly Gln Gly
```

Thr Thr Leu Thr Val Ser Ser
            115

<210> SEQ ID NO 7
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 8
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
            100                 105

<210> SEQ ID NO 10
<211> LENGTH: 119
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115

<210> SEQ ID NO 11
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
             85                  90                  95

Thr Phe Gly Gln Gly Thr Lys Val Glu Ile Lys Arg Thr Val Ala Ala
         100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
     50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asn Leu Gly Pro Ser Phe Tyr Phe Asp Tyr Trp Gly Gln Gly
         100                 105                 110

Thr Leu Val Thr Val Ser Ser Ala Ser Thr Lys Gly Pro Ser Val Phe
     115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 13
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 14
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 15
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
```

```
                130                 135                 140
Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
        210                 215

<210> SEQ ID NO 16
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```